United States Patent
Kitagawa et al.

(10) Patent No.: US 8,673,638 B2
(45) Date of Patent: Mar. 18, 2014

(54) CELL CULTURE SUPPORT AND CELL CULTURE METHOD

(75) Inventors: Fumihiko Kitagawa, Kanagawa (JP); Takafumi Imaizumi, Kanagawa (JP); Shunsuke Takei, Kanagawa (JP); Itsuki Yamamoto, Kanagawa (JP); Yasuhiko Tabata, Kyoto (JP)

(73) Assignee: Covalent Materials Corporation, Tokyo (JP)

( * ) Notice: Subject to any disclaimer, the term of this patent is extended or adjusted under 35 U.S.C. 154(b) by 118 days.

(21) Appl. No.: 13/204,324

(22) Filed: Aug. 5, 2011

(65) Prior Publication Data

US 2012/0034694 A1 Feb. 9, 2012

(30) Foreign Application Priority Data

Aug. 6, 2010 (JP) ................................. 2010-178181
Jun. 13, 2011 (JP) ................................. 2011-130953

(51) Int. Cl.
*C12N 5/0775* (2010.01)
*C12M 1/22* (2006.01)

(52) U.S. Cl.
USPC .................... 435/377; 435/395; 435/305.1

(58) Field of Classification Search
None
See application file for complete search history.

(56) References Cited

U.S. PATENT DOCUMENTS

| 5,407,001 A * | 4/1995 | Yasrebi et al. ................. 164/519 |
| 2007/0117204 A1 * | 5/2007 | Kitagawa et al. ............. 435/325 |

FOREIGN PATENT DOCUMENTS

| EP | 1 270 533 A2 | 1/2003 |
| EP | 1 970 436 | 9/2008 |
| JP | 2008-306987 | 12/2008 |
| WO | WO 01/11007 | 2/2001 |
| WO | WO 2009/154466 | 12/2009 |

OTHER PUBLICATIONS

Bosetti, M. et al., In vitro characterisation of zirconia coated by bioactive glass. Biomaterials (2001) 22: 987-994. pp. 987-990, 993.*
Takamori, E.R. et al., Effect of roughness of zirconia and titanium on fibroblast adhesion. Artificial Organs (2008) 32(4):305-309. p. 305, 308, 309.*
Diederichs, S. et al., Dynamic cultivation of human mesenchymal stem cells in a rotating bed bioreactor system based on the ZRP Platform. Biotechnology Progress 25(6):1762-1771. p. 1763.*
Chin, V.I. et al., Microfabricated platform for studying stem cell fates. Biotech. and Bioeng. (2004) 33(3):399-415; pp. 399, 404, 407.*
Definition—Linear density, Wikipedia, Linear Density, pp. 1-2; http://en.wikipedia.org/w/index.php?title=LInear_density &oldid=548303233; downloaded Apr. 12, 2013.*
Silva, T.S.N. et al., Effect of titanium surface roughness on human bone marrow cell proliferation and differentiation. An experimental study. Acta Cirurgica Brasileira 24(3):200-205 p. 200, 202, 205.*
Surface Roughness Conversion Chart (online), Copyright Engineers Edge, LLC (2000-2013). pp. 1-2; http://www.engineersedge.com/manufacturing/surface-roughness-conversion.htm; downloaded Apr. 12, 2013.*
Burns, Jorge S., et al.: "Parameters in Three-Dimensional Osteospheroids of Telomerized Human Mesenchymal (Stromal) Stem Cells Grown on Osteoconductive Scaffolds That Predict In Vivo Bone-Forming Potential," Tissue Engineering: Part A, vol. 16(7), pp. 2331-2342, 2010.
Silva, Tais Somacal Novaes, et al.: "Effect of Titanium Surface Roughness on Human Bone Marrow Cell Proliferation and Differentiation. An Experimental Study," Acta Cirurgica Brasileira, vol. 24(3), pp. 200-205, 2009.
Zhang, Nianli, et al.: "Effects of Psuedowollastonite ($CaSiO_3$) Bioceramic on In Vitro Activity of Human Mesenchymal Stem Cells," Biomaterials, vol. 31, pp. 7653-7665, 2010.
Patents Act 1977: Search Report Under Section 17 issued in corresponding United Kingdom Application No. GB1113641.3, dated Dec. 6, 2011, 5 pages.
Pittenger, Mark F., et al.: "Multillneage Potential of Adult Human Mesenchymal Stem Cells," Science, vol. 284, pp. 143-147, 1999.

* cited by examiner

*Primary Examiner* — John S Brusca
*Assistant Examiner* — Sharon M Papciak
(74) *Attorney, Agent, or Firm* — Fanelli Haag & Kliger PLLC

(57) ABSTRACT

The present invention relates to a cell culture support for culturing mesenchymal stem cells, which includes en upper surface including a plurality of wells, in which the upper surface has a root mean square roughness Rq of 100 to 280 nm and a linear density of 1.6 to 10 per 1 μm length.

11 Claims, 24 Drawing Sheets

Fig. 17

|  | Pellet method | | | Cell culture support (Opening size of 70 μm) | | | human-derived hyaline chondrocyte |
| --- | --- | --- | --- | --- | --- | --- | --- |
|  | 1W | 2W | 3W | 1W | 2W | 3W | |
| CD29 | | | | | | | |
| CD44 | | | | | | | |
| CD105 | | | | | | | |
| Col X | | | | | | | |
| Col II | | | | | | | |
| COMP | | | | | | | |
| Aggrecan | | | | | | | |
| Sox9 | | | | | | | |
| Lunx2 | | | | | | | |
| ChM1 | | | | | | | |
| GAPDH | | | | | | | |

Fig. 21
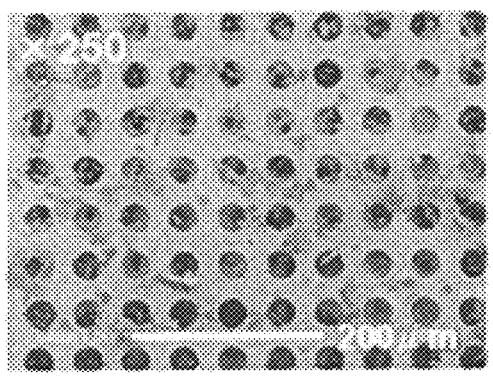
Well opening size of 30 μm
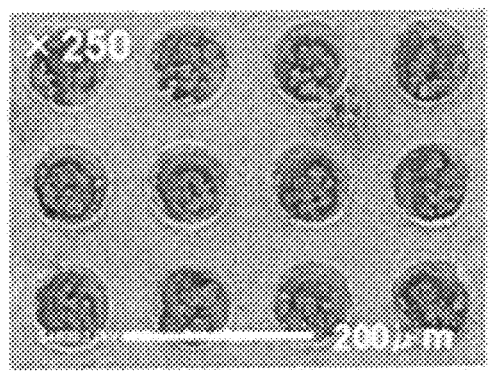
Well opening size of 70 μm
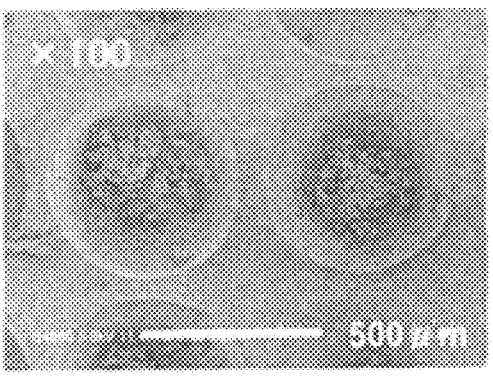
Well opening size of 540 μm
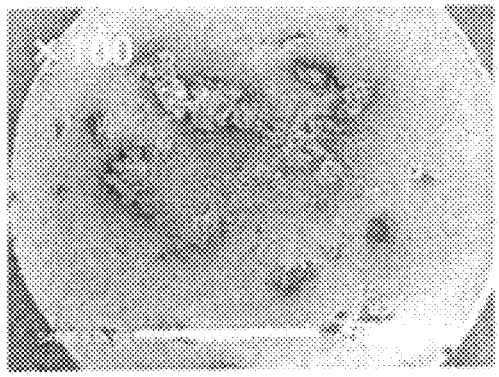
Well opening size of 1410 μm Bars:100um

CELL CULTURE SUPPORT AND CELL CULTURE METHOD

CROSS-REFERENCE TO RELATED APPLICATIONS

This application claims the benefit of Japanese Patent Application No, JP 2010-178181, filed Aug. 6, 2010, and Japanese Patent Application No. JP 2011-130953, filed Jun. 13, 2011, The disclosures of each of which are incorporated by reference herein in their entireties.

FIELD OF THE INVENTION

The present invention relates to a cell culture support which may be appropriately used to culture mesenchymal stem cell aggregates, and a cell culture method using the same.

BACKGROUND OF THE INVENTION

Mesenchymal stem cells are undifferentiated cells that exist in the mesenchymal tissues, and are known to have self-proliferation ability and differentiation ability into mesodermal cells such as osteocytes, adipocytes, and chondrocytes. Furthermore, it has been reported that mesenchymal stem cells have multipotency because they may be differentiated into non-mesodermal cells such as hepatocytes or myocardium where the heart is pulsating.

Thus, mesenchymal stem cells are expected to be used in the regenerative medicine, and clinical studies are being performed on cell therapy to transplant mesenchymal stem cells into sites where the self-renewal may not be easily achieved.

In order to differentiate mesenchymal stem cells into specific tissue cells, factors for inducing the differentiation of cells are needed. Currently, studies on specifying factors which may induce the differentiation of mesenchymal cells into bones, fat, cartilage, liver and myocardium are being performed, and the differentiation into each tissue has been efficiently induced.

The induction of the differentiation of mesenchymal stem calls is achieved by ding cells onto a petri dish and culturing them under two-dimensional conditions.

However, when the differentiation of mesenchymal stem cells is induced under this two-dimensional environment, properties of the cells become different from original properties of in vivo tissues which have a three-dimensional structure. In particular, when the induction of the differentiation of mesenchymal stem cells into cartilage is performed in a pad dish, most of the mesenchymal stem cells are known not to be differentiated into chondrocytes.

Therefore, when mesenchymal stem cells induced to differentiate into chondrocytes, the differentiation of mesenchymal stem cells in which three-dimensional aggregates are formed must be induced.

However, mesenchymal stem cells are proliferated flatways and singularly only on pew dishes, and the self-aggregating properties are not exhibited as in hepatocytes.

Therefore, methods, such as a pellet culture method, are usually used as a forted method for aggregating mesenchymal stem cells (Refer to Non-Patent Document 1).

In addition, a culture method using a three-dimensionally shaped culture support having a plurality of concave portions is also considered as described in Patent Document 1.

However, a pellet culture method described in Non-Patent Document 1 is a method for aggregating cells by adding a suspension of the cells to a 15 ml centrifuge tube and precipitating the cells forcibly by centrifugation, and it has been difficult to obtain good cell aggregates because mechanical stimuli on cells are strong so that the cells are damaged.

In addition, when aggregated mesenchymal stem cells are induced to differentiate into chondrocytes by a pellet culture method, expression of Type II collagen or aggrecan which is a gene expressed by in vivo chondrocytes (hyaline chondrocytes) may be identified.

However, the expression of Type X collagen which is exp by further differentiating hypertrophic chondrocytesor CD105 specific to mesenchymal stem cells may be also identified and thus there is a problem in that the aggregate cannot be induced to differentiate into uniform cartilage tissues having the same properties in an in vivo tissue.

In addition, when a three-dimensionally shaped culture support having a plurality of concave portions as described in Patent Document 1 is used there is a problem in that mesenchymal stem cells cannot be aggregated only into concave portions and thus the same properties cannot be obtained in an in vivo tissue, and the induction of differentiation into a tissue having more uniform differentiation conditions cannot be achieved.

Thereto there is a need for a cell culture support and a cell culture method in which a cell aggregate can be formed by stationary culture of mesenchymal stem cells to thereby be induced to differentiate into a tissue which has the same properties and has uniform differentiation conditions in in vivo tissues.

[Patent Document 1] JP-A-2008-306987
[Non-Patent Document 1] Mark F, Pitternger et al., Science, 284, 1999, p. 143-146

SUMMARY OF THE INVENTION

The present invention his been made in order to solve the above problems. An object of the present invention is to provide a cell culture support which may efficiently obtain a great amount of cell aggregates which have the same properties in an in vivo tissue and are uniform in terms of differentiation state by aggregating mesenchymal stem cells three-dimensionally into a simple and uniform shape, and a cell culture method using the same.

The present invention rtes to a cell culture support for culturing mesenchymal stem cells, which comprises an upper surface comprising a plurality of wells, wherein the upper surface has a root mean square surface roughness Rq of 100 to 280 nm and a linear density of 1.6 to 10 per 1 μm length.

C.) manufactured by using a zirconia raw material powder (powder pre-sintered at 1,150° C.) according to Test Example 1-2.

Figure 5:
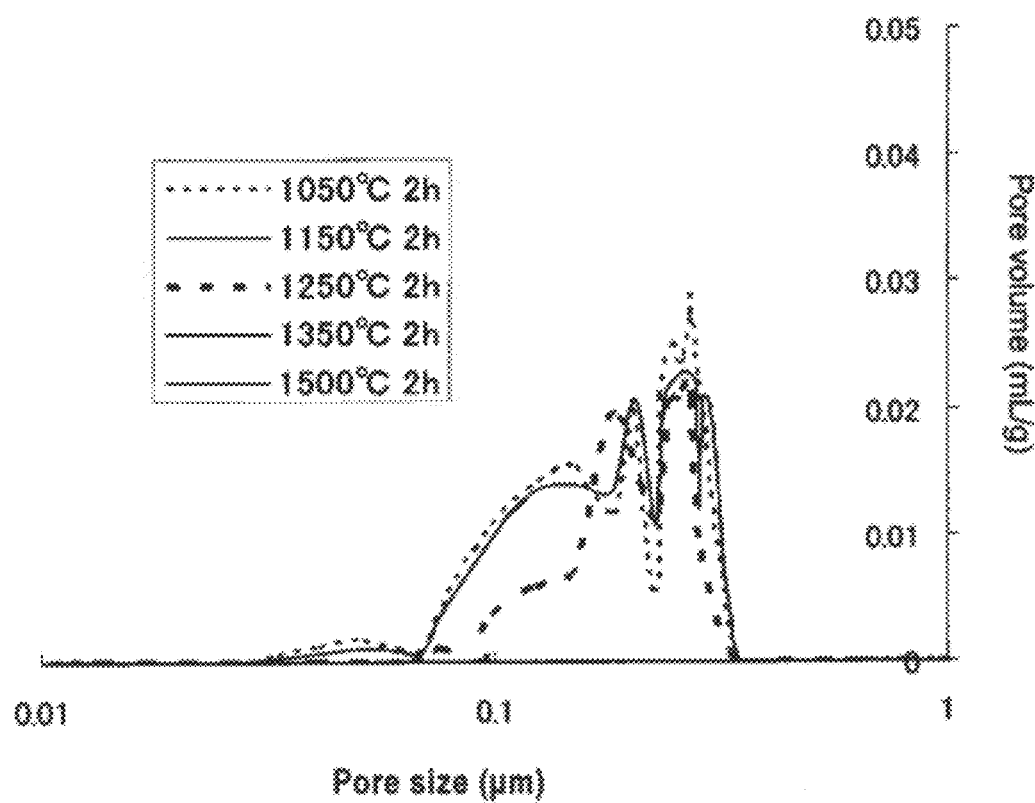

FIG. 5 is a pore size distribution of a zirconia cell culture support (sintered at 1,050° C. to 1,500° C.) manufactured by using a zirconia raw material powder (powder pre-sintered at 1,150° C.) according to Test Example 1-2, measured by mercury intrusion porosimetry.

Figure 6:
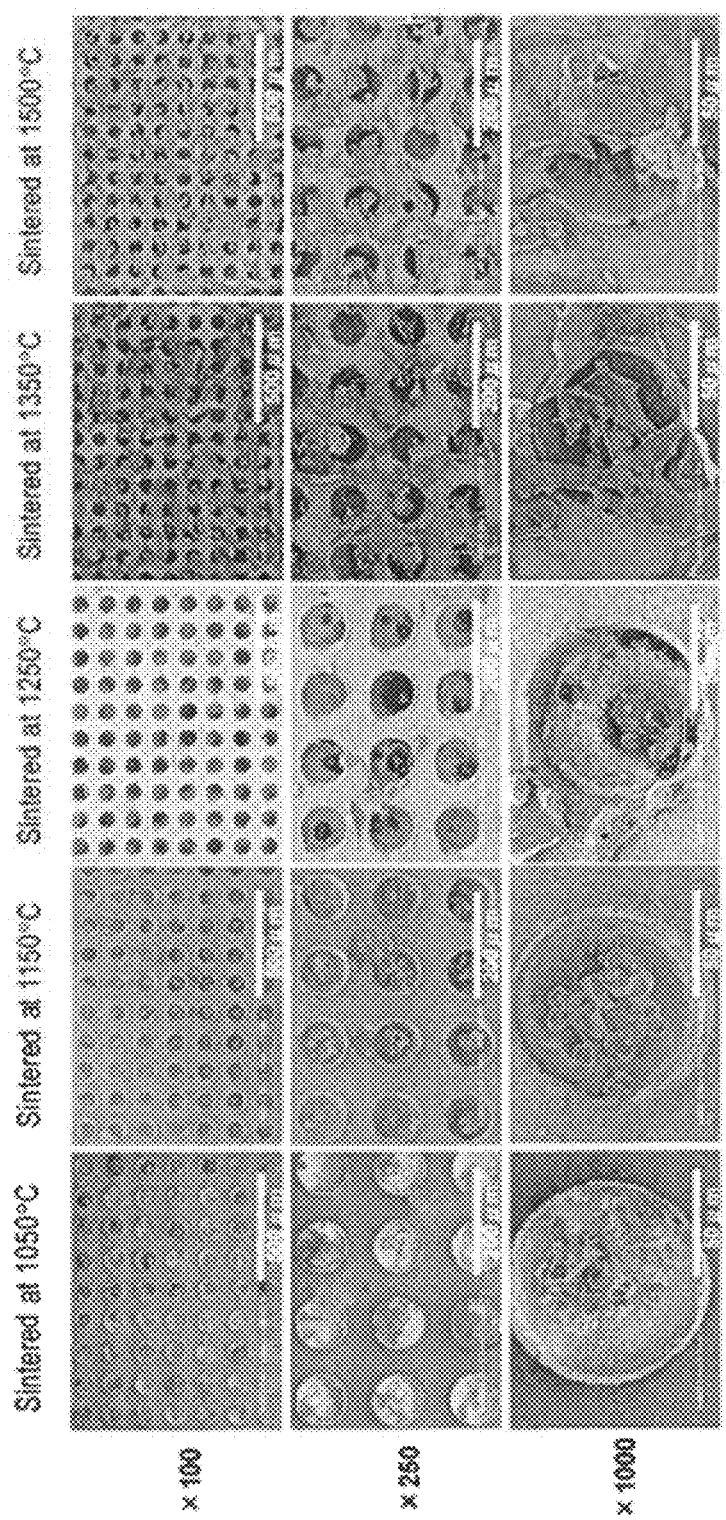

FIG. 6 is a group of SEM photos (x100, x250, and x1,000) of hMSCs cultured on a zirconia cell culture support (sintered at 1,050° C. to 1,500° C.) manufactured by using a zirconia raw material powder (powder pre-sintered at 1,150° C.) according to Test ample 1-2.

Figure 7:
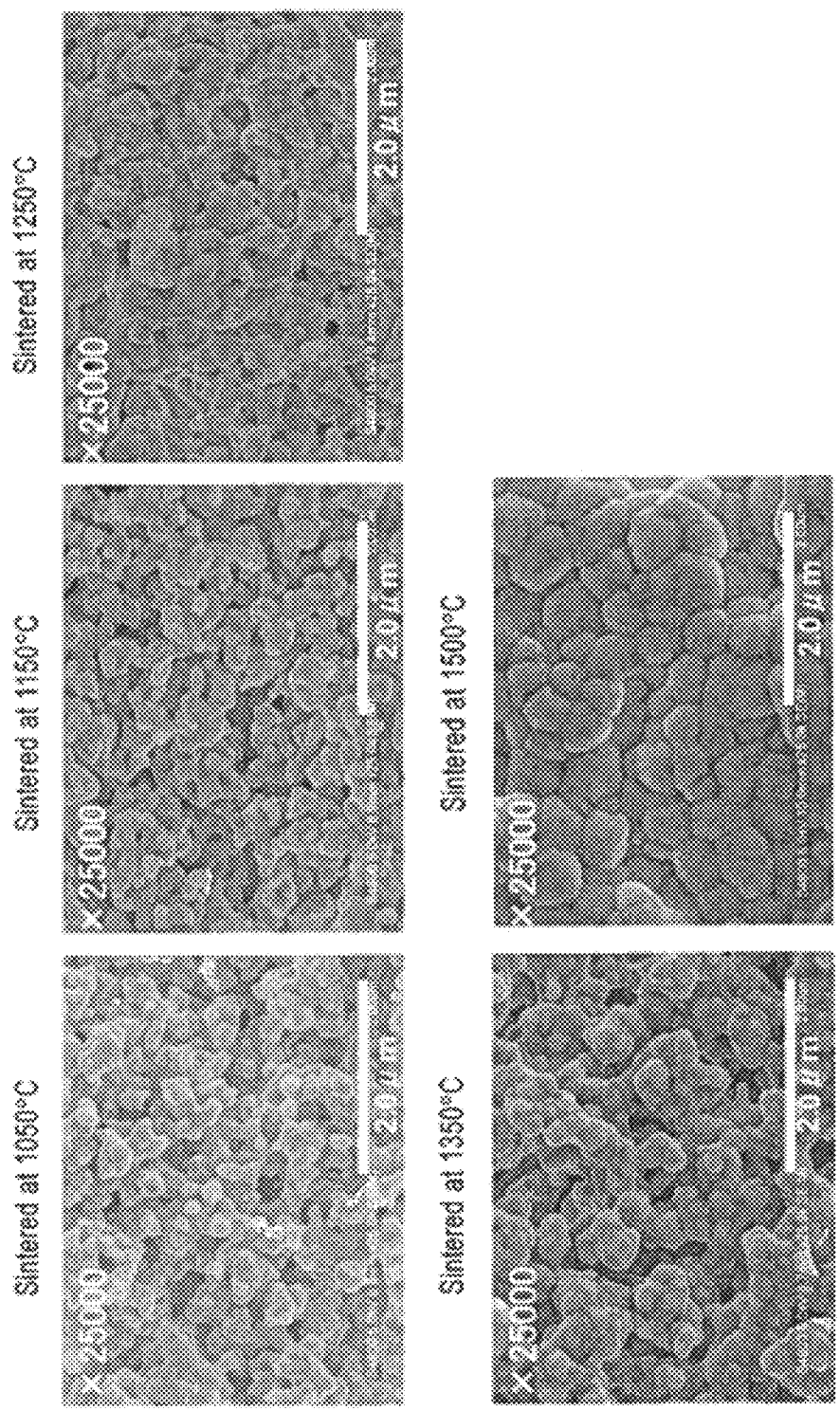

FIG. 7 is an SEM photo (x25,000) of the surface skeleton of a zirconia cell culture support (sintered at 1,050° C. to 1,500° C.) manufactured by using a zirconia raw material powder (powder pre-sintered at 1,250° C.) according to Test Example 1-3.

Figure 8:
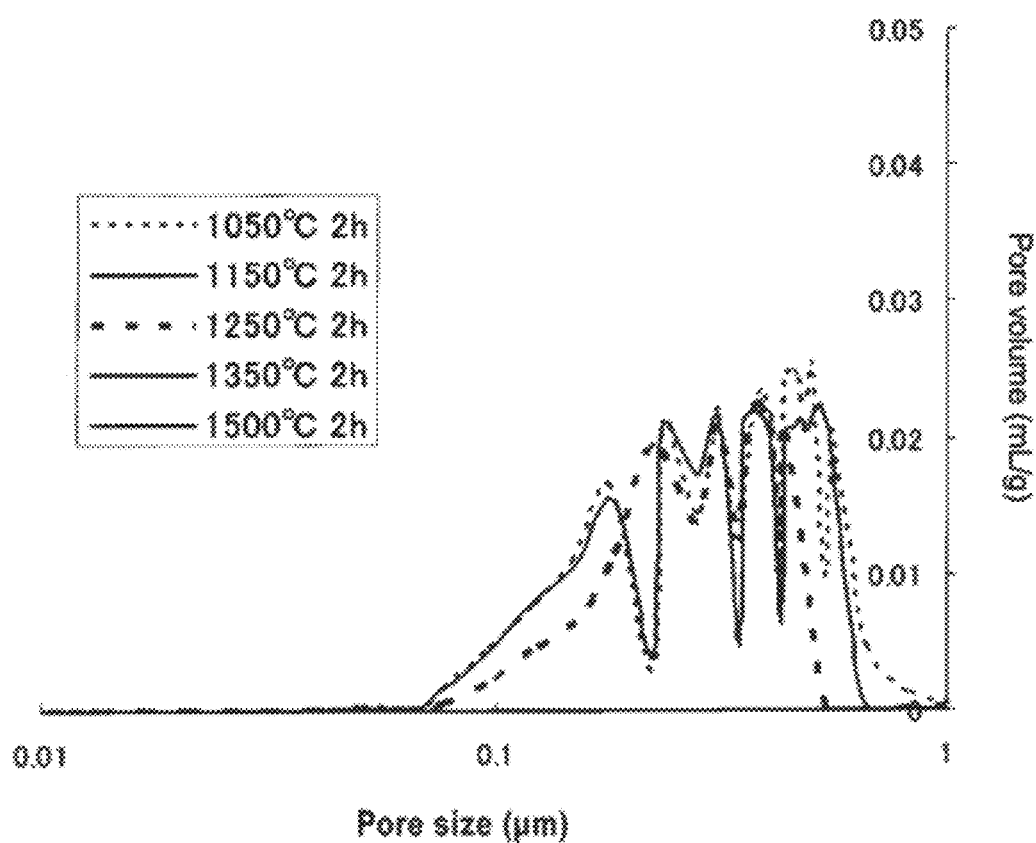

FIG. 8 is a pore size distribution of a zirconia cell culture support (sintered at 1,050° C. to 1,500° C.) manufactured by using a zirconia raw material powder (powder pre-sintered at 1,250° C.) according to Test Example 1-2, measured by mercury intrusion porosimetry.

Figure 9:
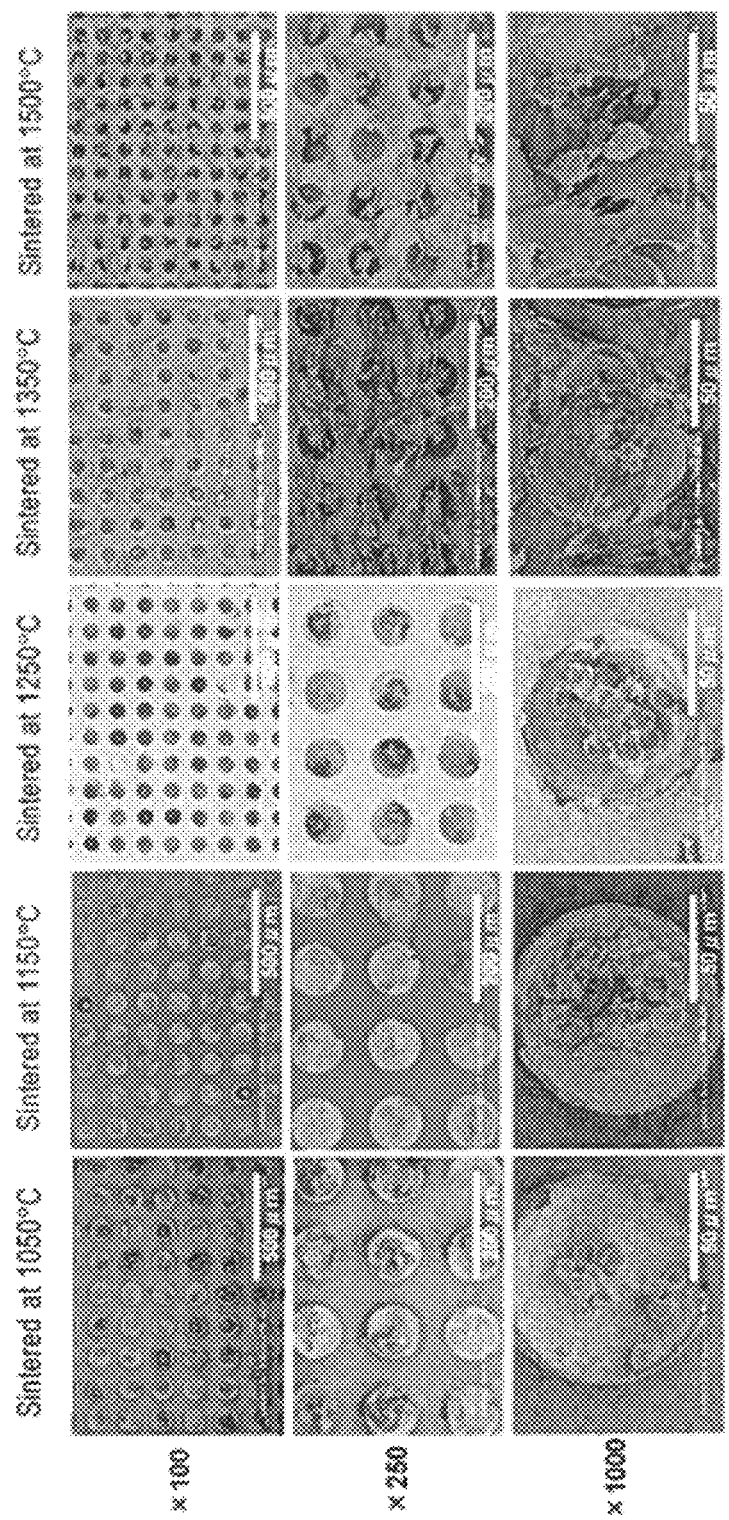

FIG. 9 is a group of SEM photos (x100, x250, and x1,000) of hMSCs cultured on a zirconia cell culture support (sintered at 1,050° C. to 1,500° C.) manufactured by using a zirconia raw material powder (powder pre-sintered at 1,250° C.) according to Test Example 1-3.

Figure 10:
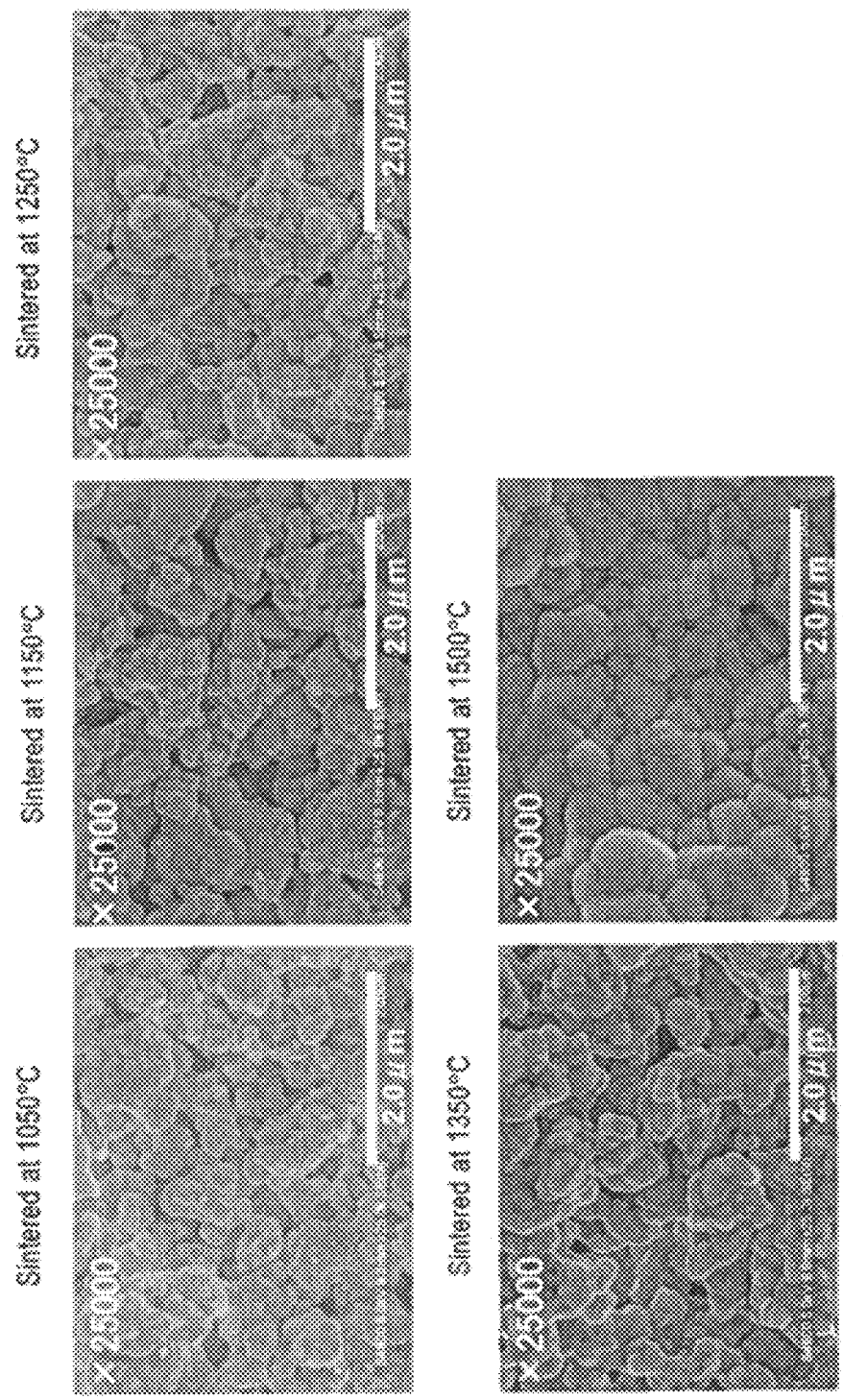

FIG. 10 is a SEM photo (x25,000) of the surface skeleton of a zirconia cell culture support (sintered at 1,050° C. to 1,500° C.) manufactured by using a zirconia raw material powder (powder pre-sintered at 1,350° C.) according to Test Example 1-4-4.

Figure 11:
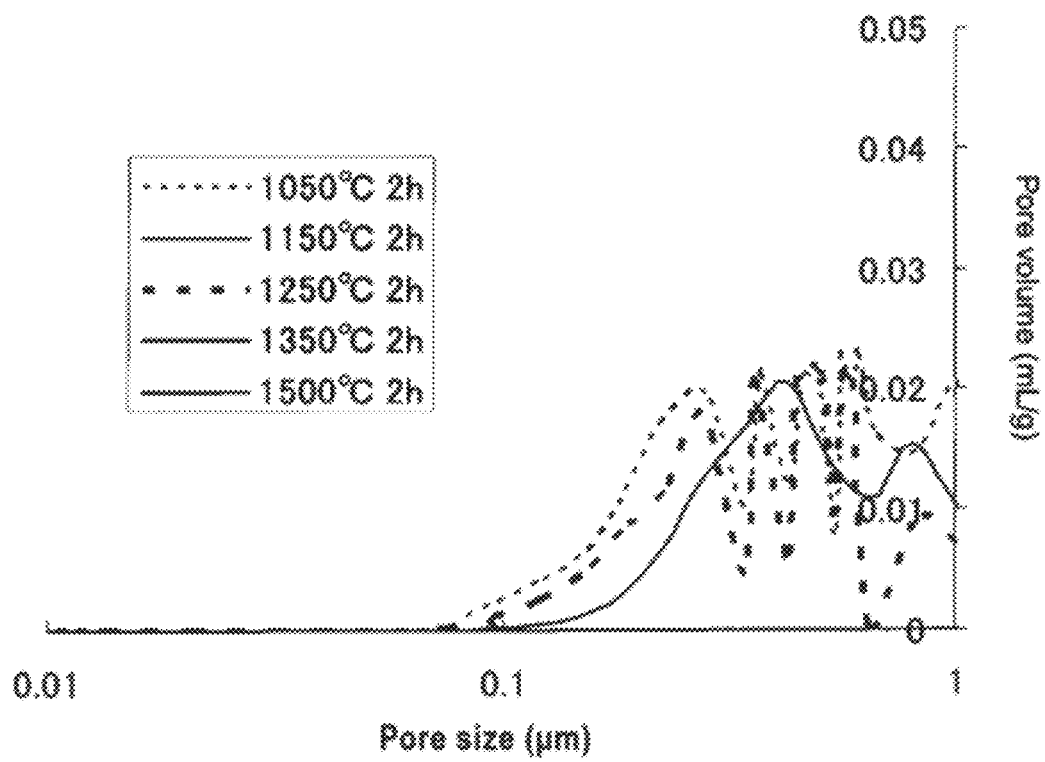

FIG. 11 is a pore size distribution of a zirconia cell culture support (sintered at 1,050° C. to 1,500° C.) manufactured by using a zirconia raw material powder (powder pre-sintered at 1,350° C.) according to Test Example 1-4, measured by mercury intrusion porosimetry.

Figure 12:
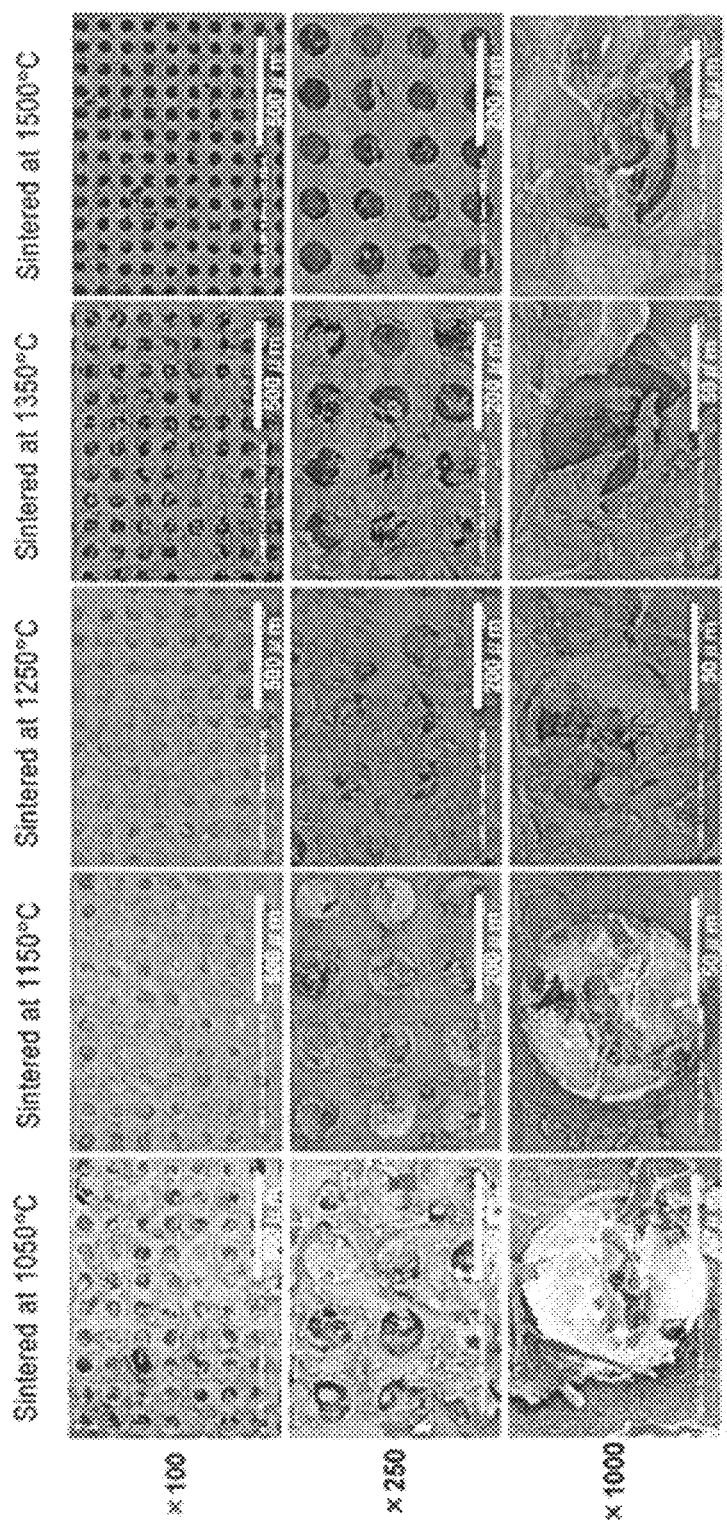

FIG. 12 is a group of SEM photos (x100, x250, and x1,000) of hMSCs cultured in a zirconia cell culture support (sintered at 1,050° C. to 1,500° C.) manufactured by using a zirconia raw material powder (powder pre-sintered at 1,350° C.) according to Test Example 1-4.

Figure 13:
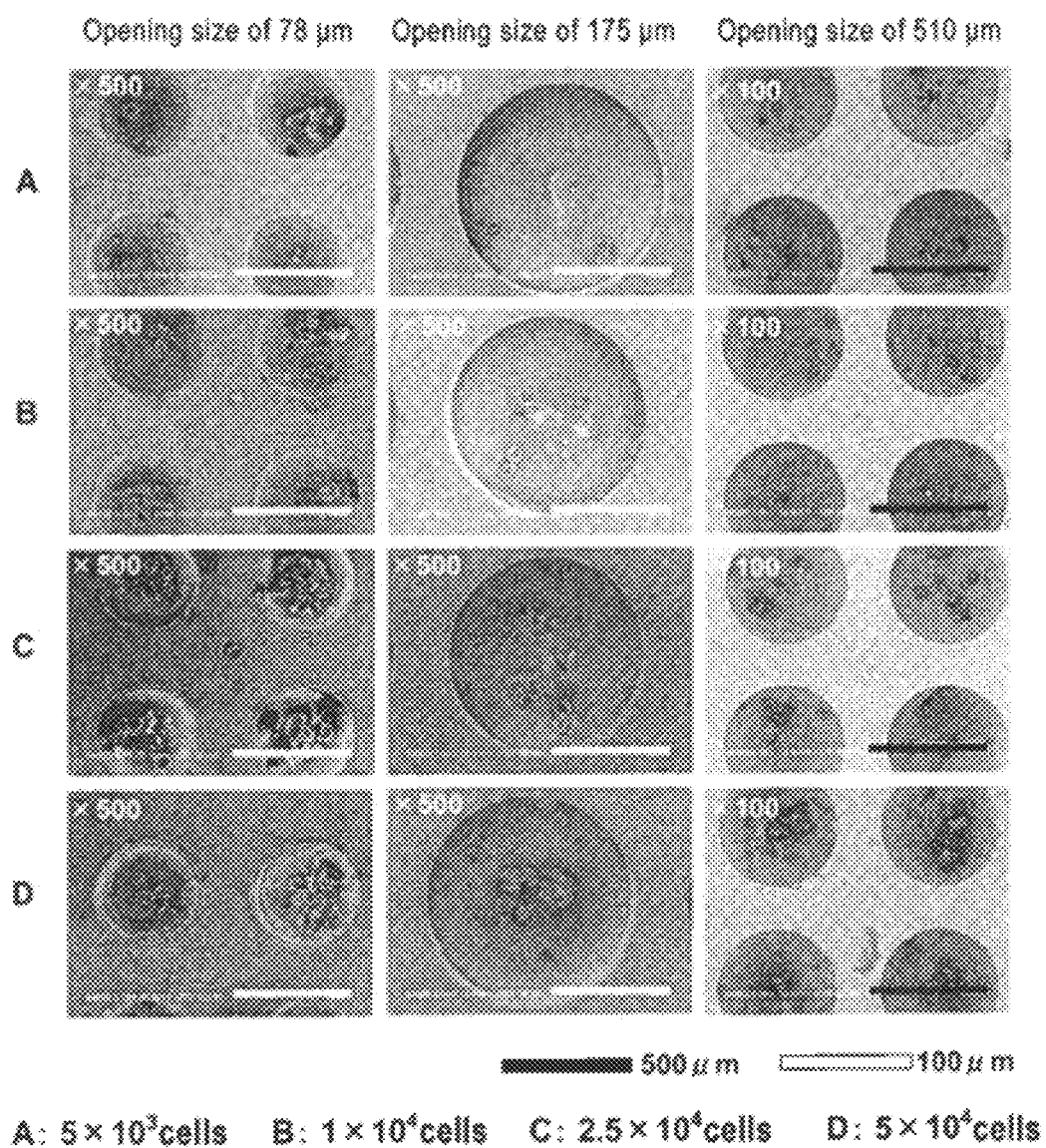

FIG. 13 of SEM photos (well opening sizes of 78 μm and 175 μm: x500 and a well opening size of 510 μm: x100) of human mesenchymal stem cells (hMSCs) cultured on a zirconia cell culture support (sintered at 1,150° C.) with wells having opening sizes of 78 μm, 175 μm, and 510 μm) arranged according to Example 1.

Figure 14:
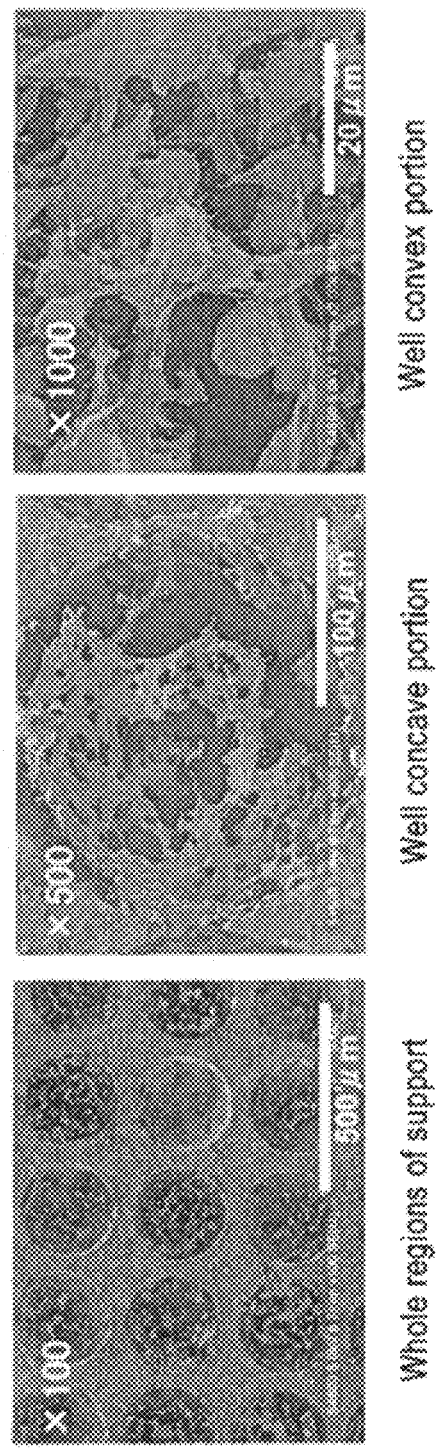

FIG. 14 is a group of SEM photos (whole regions of the support: x100, a well concave portion: x500, and a well convex portion: x1,000) of HepG2 cultured on a cell culture support (sintered at 1,150° C.) with wells having an opening size of 175 μm arranged according to Comparative Example 1.

Figure 15:
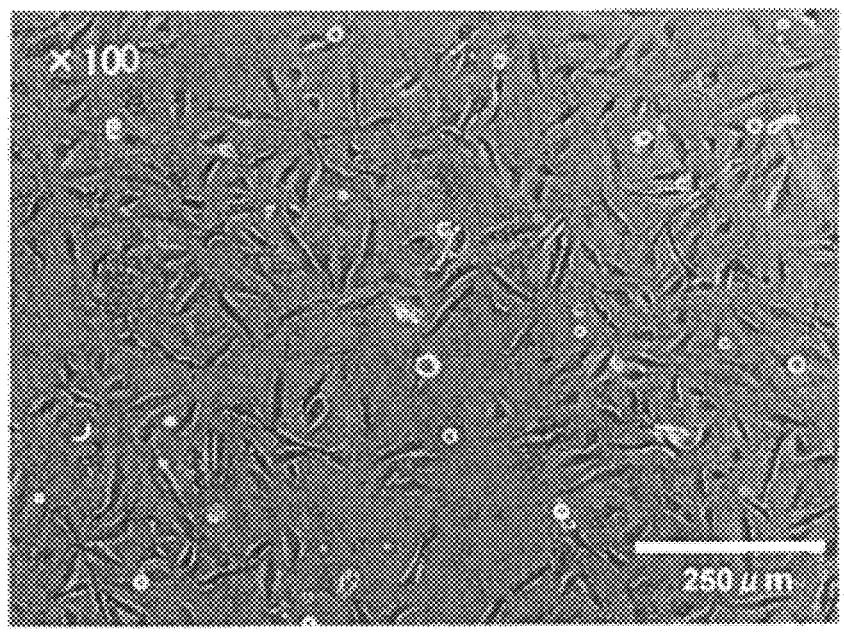

FIG. 15 is microscopic photo (x100) of hMSCs cultured in a petri dish according to Comparative Example 2.

Figure 16:
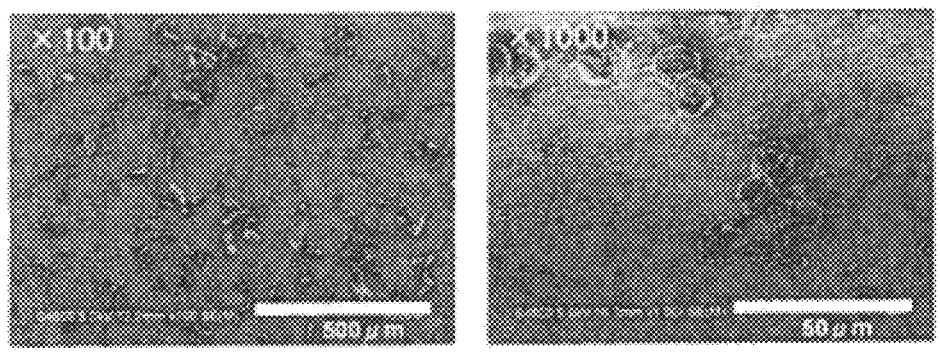

FIG. 16 is an SEM photo of cells cultured on a zirconia plate (at 150° C.) according to Comparative Example 3, FIG. 17 illustrates a comparison of a marker for an expression gene in each tissue, which induces the differentiation of hMSC aggregates formed on a zirconia cell culture support or by a pellet method into chondrocytes for 1, 2, and 3 weeks (1W, 2W, 3W) with a marker for an expression gene of a human-derived hyaline chondrocyte, in Example 2 and Comparative Example 4.

Figure 18:
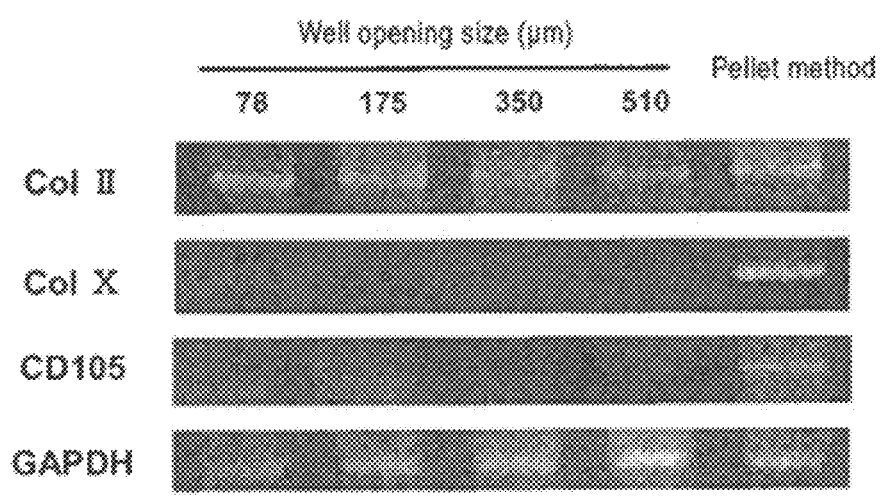

FIG. 18 illustrates a comparison of markers for an expression gene in each tissue, which induces the differentiation of hMSC aggregates formed on zirconia cell culture supports with well opening sizes of 78 μm, 175 μm, 350 μm, and 510 μm or by a pellet method into chondrocytes, in Example 3.

Figure 19:
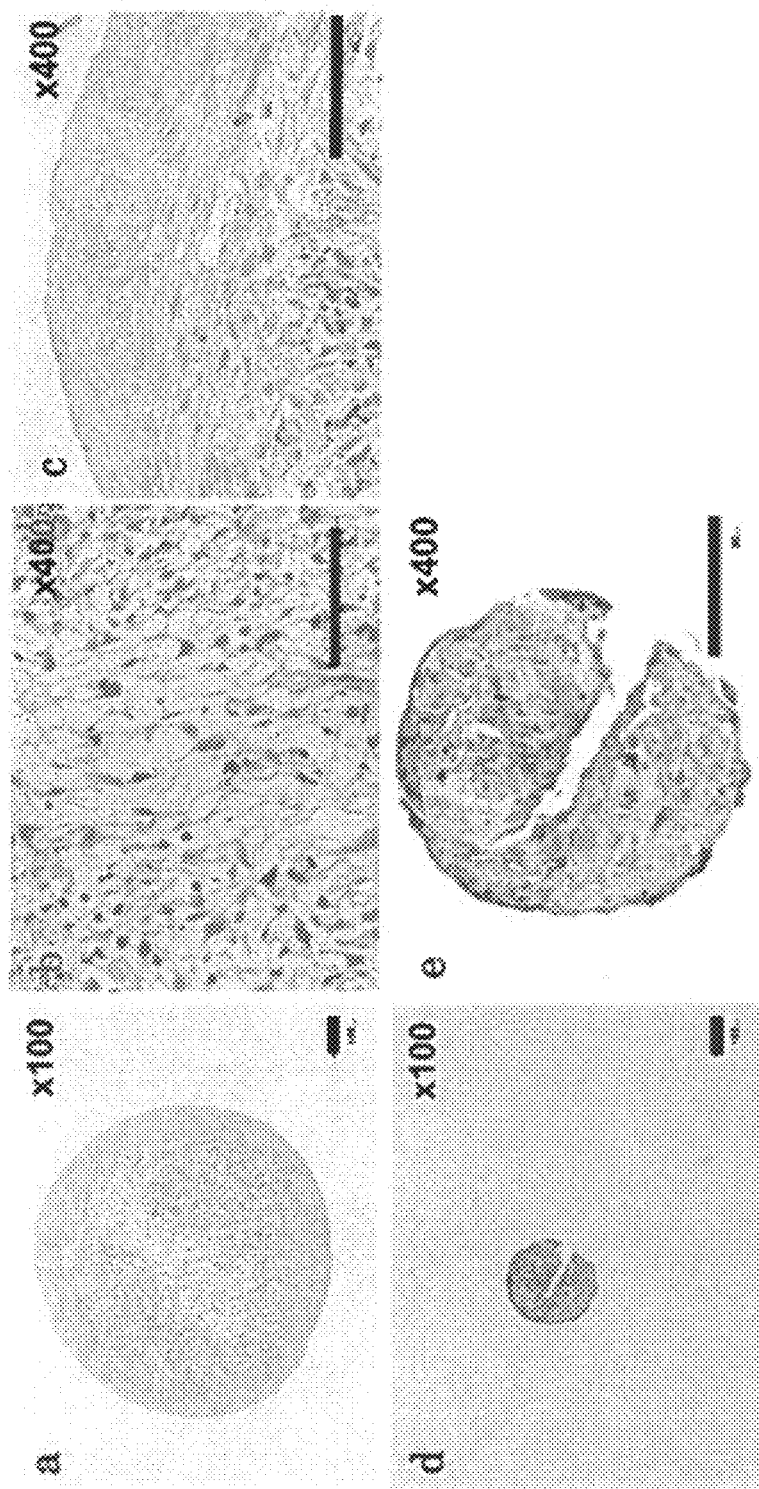

FIG. 19 is a group of microscopic photos (a. pellet method: x100, b. pellet method cartilage tissue central portion): x400, c. pellet method (outer side of a cartilage tissue): x400, d. a cell culture support with a well opening size of 510 μm: x100, and e. a cell culture support with a well opening size of 510 μm: x400) of cartilage tissue which are obtained by inducing the differentiation of hMSC aggregates formed on a zirconia call culture support or by a pellet method, stained with Safranin O in Example 4 and Comparative Example 5.

Figure 20:
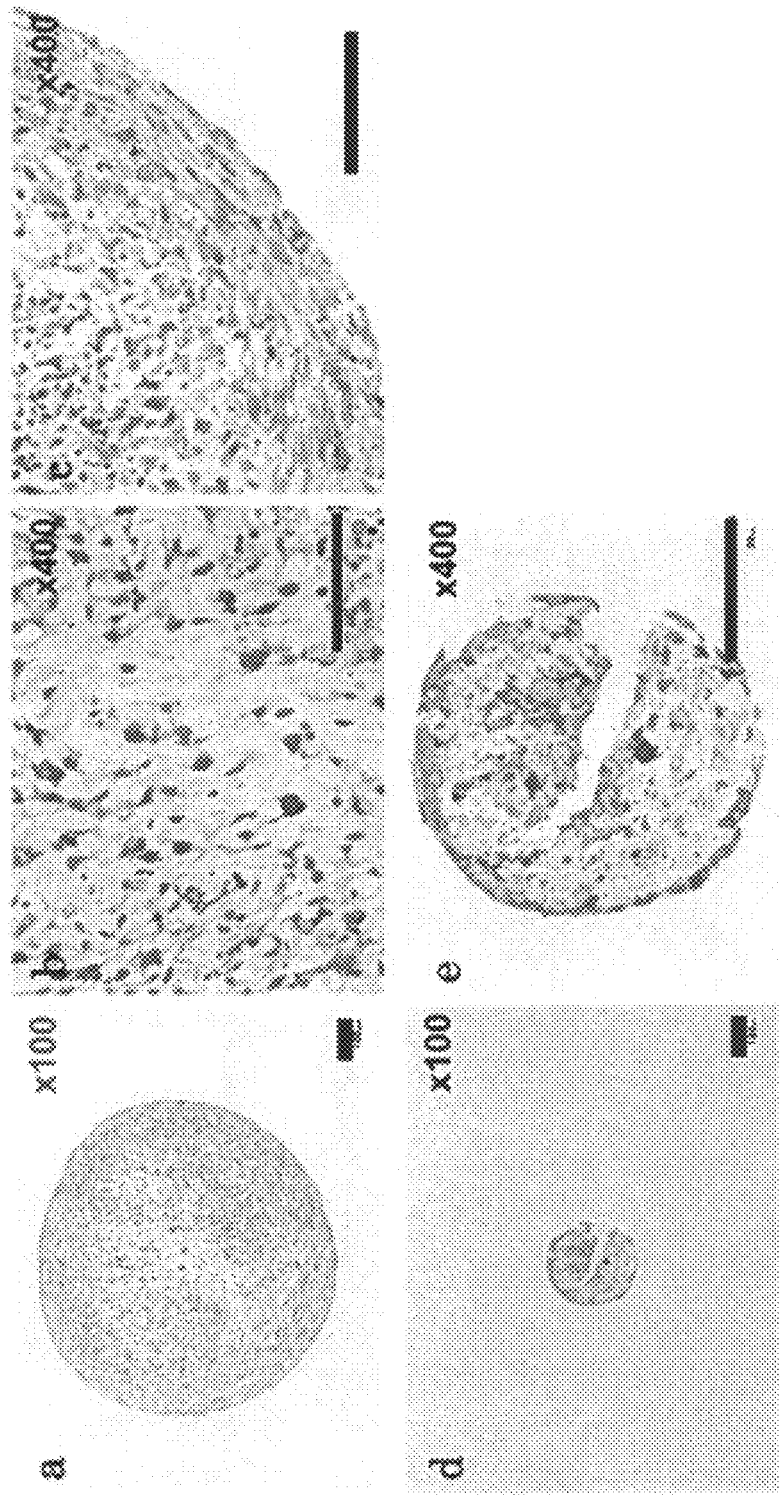

FIG. 20 is a group of microscopic photos (a. pellet method: x100, b. pellet method (cartilage tissue central portion): x400, c. pellet method (outer side of a cartilage tissue): x400, d. a cell culture support with a well opening size of 510 μm: x100, and e. a call culture support with a well opening size of 510 μm: x400) of cartilage tissue which are obtained by inducing the differentiation of hMSC aggregates formed on a zirconia cell culture support or by a pellet method, stained with toluidine blue in Example 4 and Comparative Example 5.

FIG. 21 is a group of SEM photos (well opening sizes of 30 μm and 70 μm: x250 and well opening sizes of 540 μm and 1,410 μm: x100) of hMSCs cultured on cell culture supports (well opening sizes of 30 μm, 70 μm, and 1,410 μm).

Figure 22:
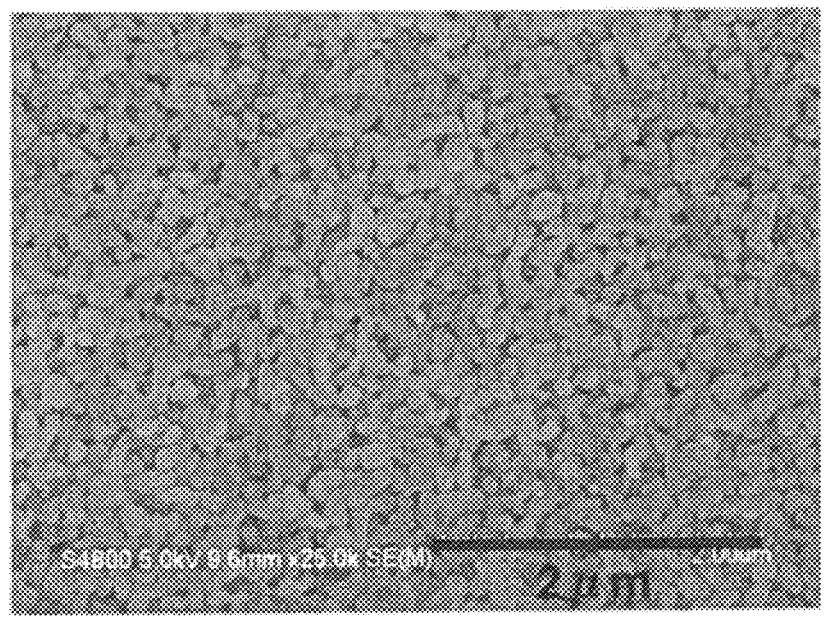

FIG. 22 is an SEM photo (x25,000) of the surface skeleton of an alumina cell culture support manufactured by using an alma raw material powder according to Comparative Example 6.

Figure 23:
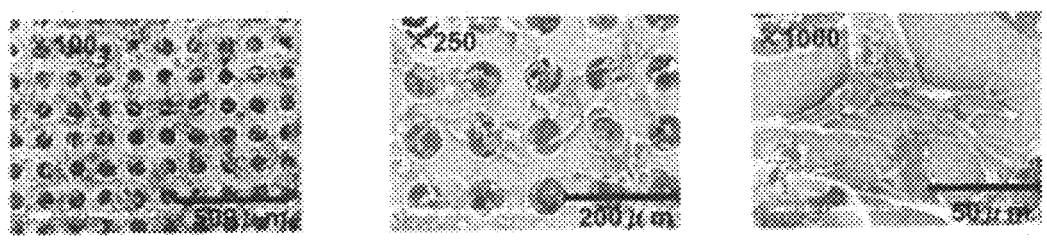

FIG. 23 is a group of SEM photos (x100, x250, and x00) of hMSCs cultured on an alumina cell culture support with wells having an opening size of 80 μm arranged according to Comparative Example 6.

Figure 24:
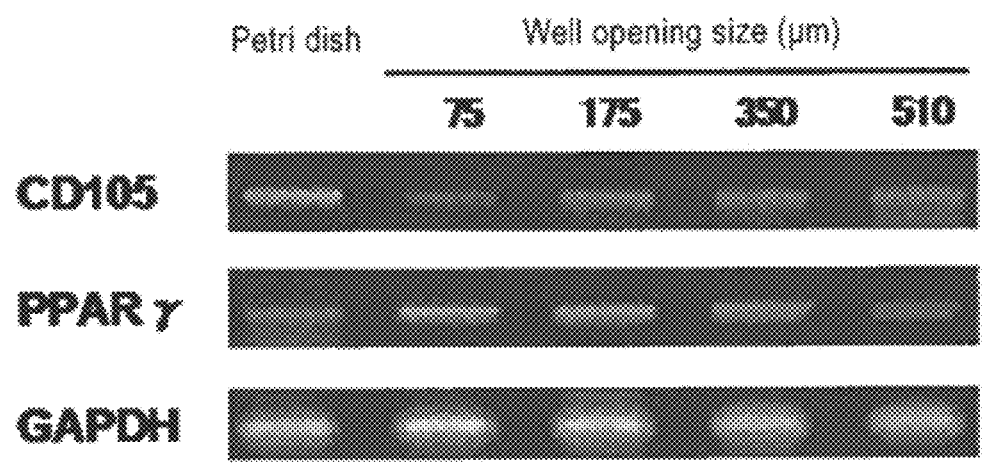

FIG. 24 illustrates a comparison of markers for an expression gene in each tissue, which induces the differentiation of hMSC aggregates formed on a zirconia cell culture support or on a petri dish into adipocytes. in Example 5 and Comparative Example 7.

Figure 25:
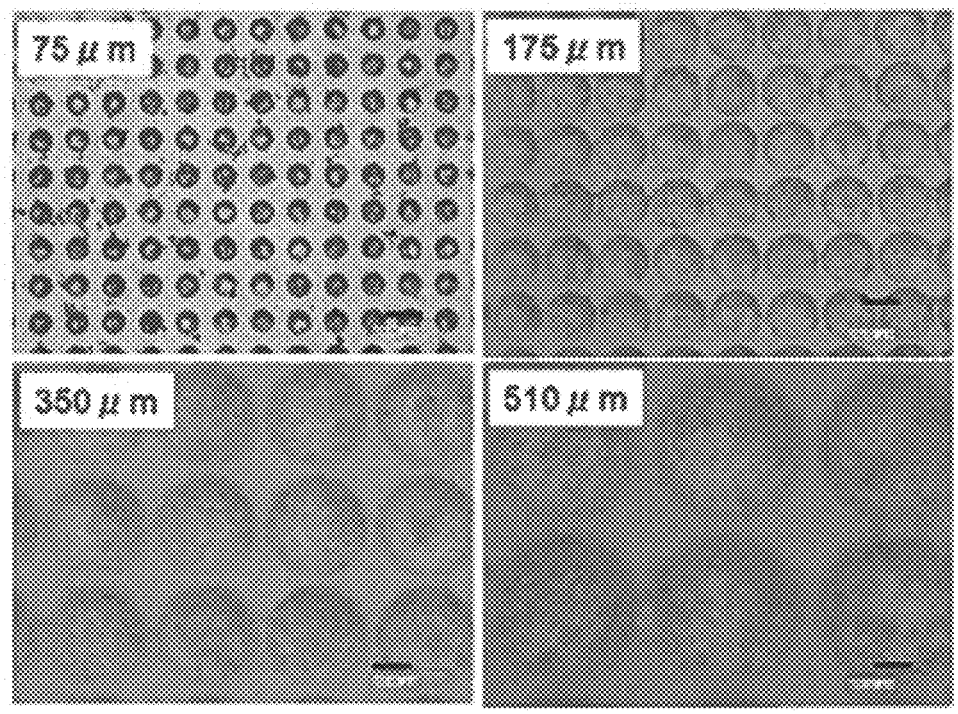

FIG. 25 is a microscopic photo (x100) of adipocytes obtained by inducing the differentiation of hMSC aggregates formed on a zirconia cell culture support, stained with Oil Rod O in Example 5.

Figure 26:
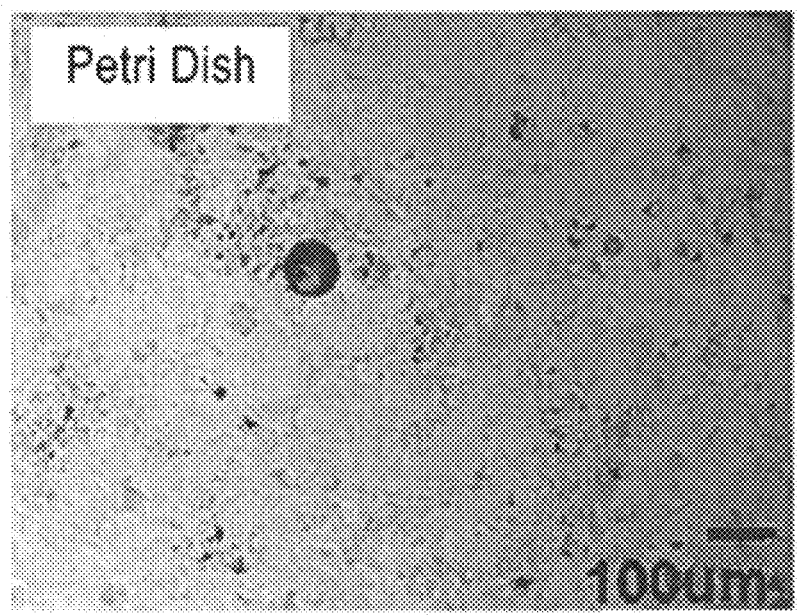

FIG. 26 is a microscopic photo x100) of adipocytes obtained by inducing the differentiation of hMSC aggregates formed on a petri dish, stained with Oil Red O in Comparative Example 7.

Figure 27:
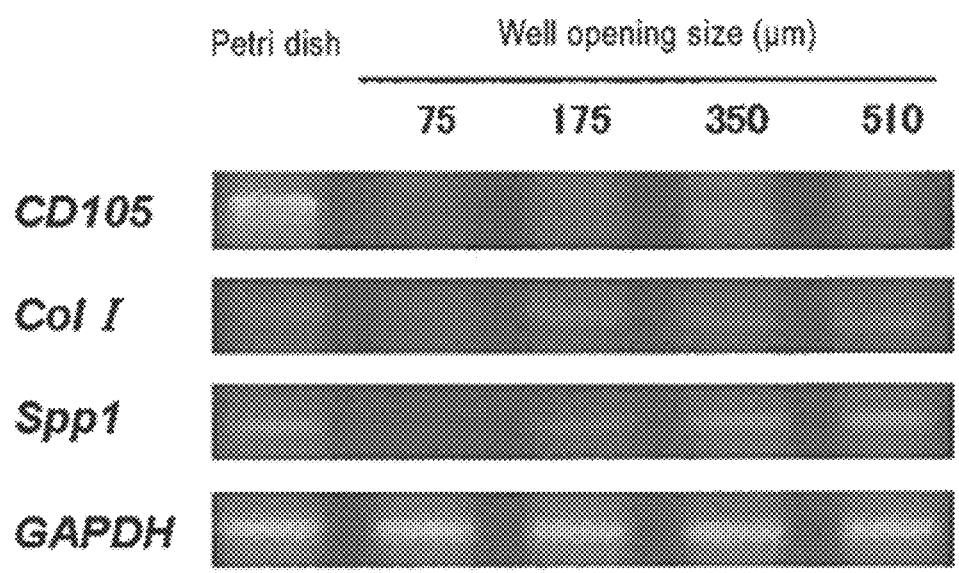

FIG. 27 illustrates a comparison of markers for an expression gene each tissue, which induces the differentiation of hMSC aggregates formed on a zirconia cell culture support or on a petri dish into osteoblasts, in Example 6 and Comparative Example 8.

DETAILED DESCRIPTION OF THE INVENTION

A spherical shape may be maintained because a support having this surface state at the upper surface is used and thus squamous mesenchymal stem cells are not attached to the upper surface. Otherwise, even in the case of mesenchymal stem cells attached to the upper surface to be planarized in the initial phase of the culturing of mesenchymal stem cells, the squamous mesenchymal stem cells become spherical when a certain time passes. Furthermore, since a plurality of wells are formed on the upper surface, spherical mesenchymal stem cells may migrate to the wells and be aggregated to efficiently culture a great amount of mesenchymal stem cell aggregates, and mesenchymal stem cells may be efficiently induced to differentiate into tissue cells such as hyaline chondrocytes, adipocytes or osteoblasts, which are similar to in vivo tissues in properties.

In the cell culture support, the wells preferably have openings with a circular or rectangular shape and an opening size of 70 to 550 μm range.

These well shapes and well opening sizes may be used to control the three dimensional structuring of mesenchymal stem cell aggregates and their sizes more appropriately during the culturing in the well. In addition, even in the case of induction of differentiation into hyaline chondrocytes, in vivo tissues such as chondrocytes which are more uniform in the differentiation state may be obtained.

The bottom surfaces of the wells preferably have a root mean square average roughness Rq of 100 to 280 nm and a linear density of 1.6 to 3.0 per 1 μm length.

When the bottom surfaces of the wells have at least a surface roughness similar to the upper surface of the support, squamous cells are not attached to the bottom surface of the well, and cells adhered to the well bottom may become easily spherical to form cell aggregates easily.

In addition, a distance from a central point of the wells disposed adjacent to each other is preferably 80 to 700 μm.

The distance may allow cells to place wells efficiently and stably supply oxygen or nourishment to aggregated cell aggregates in the well.

Also, preferably, the cell culture support is formed of sintered ceramics, and the sinter ceramics have an average pore size of 0.15 to 0.45 μm.

When the support is sintered ceramics, the upper surface having the above surface roughness can be easily formed. The above average pore size can provide cell aggregates formed in the well with differentiation-inducing factors, nourishment, oxygen, and the like to cell aggregates formed in the well efficiently from the other surface of the support.

For en efficient culturing of mesenchymal stem cell aggregates, zirconia is preferably used as the ceramics.

When zirconia is used as the ceramics, the resistance to modification of mesenchymal stem cells can be suppressed in such conditions that a culture medium is present on the surface of the support.

The upper surface of the cell culture support is preferably a non-processed surface after sintering of ceramics with less planarization, considering properties of cells which recognize the unevenness of ceramics particles contacted to change their shapes.

Also, the cell culture method according to the present invention relates to a cell culture method using the above cell culture support, which comprises:

disposing an upper surface of the cell culture support upwardly in a container, supplying a first culture medium to the container to permeate the first culture medium by the capillary action to the well opening of the cell culture support;

adding a second culture medium including undifferentiated mesenchymal stem cells dropwise to the upper surface of the cell culture support into which the first culture medium is permeated to seed mesenchymal stem cells;

supplying the first culture medium to the container to immerse the cell culture support as a whole in the first culture medium and to proceed aggregation of the mesenchymal stem cells in the well;

discharging the first culture medium and the second culture medium except for the mesenchymal stem cells out of the container; and supplying a third culture medium for inducing of differentiation of the mesenchymal stem cells which are aggregated into tissue cells, such as hyaline chondrocytes, adipocytes and osteoblasts, to the container to immerse the cell culture support as a whole in the third culture medium to induce differentiation of the mesenchymal stem cells into any tissue cell of hyaline chondrocytes, adipocytes and osteoblasts in the well.

According to the culture method, the formation of mesenchymal stem cell aggregates and the induction of the differentiation from the aggregates into tissue cells such as hyaline chondrocytes, adipocytes and osteoblasts, may be conducted simply or efficiently as in the same support.

The number of mesenchymal stem cells in the second culture medium is preferably from $1 \times 10^4$ to $1 \times 10^6$ per 1 cm$^2$ of the support According to the above culture method, a plurality of cells permeate into the well easily so that cell aggregates can be formed more efficiently.

According to the cell culture support in the present invention, mesenchymal stem cells can be simply aggregated in a uniform three dimensional shape and obtain a great amount of cell aggregates with the same properties in an in vivo tissue.

Also, according to the cell culture method in the present invention using the cell culture support may be used to conduct the formation of mesenchymal stem cell aggregates and the induction of the differentiation from the aggregates into tissue cells such as hyaline chondrocytes, adipocytes and osteoblasts can be carried out in the same support simply and efficiently, and cartilage tissue in a uniform differentiation state may be obtained.

Hereinafter, the present invention will be described in more detail with reference to drawings.

The cell culture support according to the present invention is used for culturing mesenchymal stem cells and has a plurality of wells for culturing cells formed on the upper surface. In addition, the upper surface has a predetermined surface roughness.

Calls applied to the present invention are mesenchymal stem cells (MSCs), and specifically mesenchymal stem cells which may be obtained from bona marrow, umbilical cord blood, fat, and the like or tissue-derived progenitor cells, and immortalized cells thereof.

The cell culture support according to the present invention may form a great amount of aggregates of mesenchymal stem cells in this uniform shape efficiently and induce the differentiation of mesenchymal stem cells into tissue cells such as hyaline chondrocytes, adipocytes and osteoblasts efficiently.

Specifically, the upper surface of the support has a root mean square average roughness Rq of 100 to 280 nm and a linear density of 1.6 to 3.0 per 1 μm length.

A spherical shape may be maintained because a support having this surface state at the upper surface is used and thus squamous mesenchymal stem calls are not attached to the upper surface. Otherwise, even in the case of mesenchymal stem cells attached to the upper surface to be planarized in the initial phase of the culturing of mesenchymal stem cells, the squamous mesenchymal stem cells become spherical when a certain time passes. Furthermore, since a plurality of wells are formed on the upper surface, spherical mesenchymal, stem cells may migrate to the wells and be aggregated to efficiently form and culture a great amount of mesenchymal stem cell aggregates, and the differentiation into tissue cells such as hyaline chondrocytes, adipocytes or osteoblasts, which corresponds to in vivo tissues in properties, may be efficiently induced from mosenchymal stem cells.

When the root mean square average roughness Rq and the linear density are out of the ranges, the cell tends to be planarized and adhered to the upper surface of the support and not to form cell aggregates.

Although the causes are not clarified, they are expected to be due to the following phenomena.

When the upper surface of the support has a surface state with a large flat surface or a minimum flat surface of a predetermined area, mesenchymal stem cells are planarized and closely adhered. However, in the case of a specific uneven surface without this flat surface, a spherical shape may be maintained with mesenchymal stem cells without being planarized. A plurality of wells are also present at the upper surface of the support, and thus their spherical mesenchymal stem cells migrate to the wells and are aggregated. In particular, it is considered important for a minimum flat surface not to be present on the upper surface of the convex portion in an uneven shape in the upper surface of the support.

The root mean square average roughness Rq and linear density are parameters for defining the surface roughness.

As used herein, the linear density is a parameter in a surface direction, and indicates the number of a roughness curve crossing an average surface per μm of the length.

In the present invention, the root mean square average roughness Rq is measured by JIS B 0601.

In addition, the linear dimity is measured with a scale of 0.8 μm and a scan size of 10 μm×10 μm by atomic force microscopy (AFM).

The well formed at the upper surface has an opening in a circular or rectangular shape, and an opening size of 70 to 550 μm range.

The well opening is preferably a circular or rectangular shape in view of easiness of seeding of cells and forming of cell aggregates, easiness of processing of wells, and the like.

As used herein, the opening size of the well when the opening is in the form, of a circle and a rectangle refers to a diameter of the circle and a distance between edges facing each other, respectively. When the opening is in the form of a polygon, the opening size refers to a distance between an edge and a parallel line through an opposite apex.

In addition, when aggregates of mesenchymal stem cells are induced to differentiate into tissue cells such as chondrocytes, adipocytes and osteoblasts by culturing on a support with a well opening size in the above range, the differentiation of the aggregates of the mesenchymal stem cells may be induced while their size is being controlled more precisely as it is. Compared to conventional differentiation-inducing methods such as a pellet method, aggregates of mesenchymal stem cells are close to tissue cells such as in vivo chondrocytes in properties, and thus various kinds of cells are not incorporated and in vivo tissues such as cartilage tissue with a more uniform differentiation state may be obtained.

Furthermore, in terms of a size control of cell aggregates, the depth of the well is preferably from 70 to 500 μm in the same manner as the well opening. When the well opening size is less than 70 μm or more than 550 μm, it is difficult for mesenchymal stem cells to form a desired three-dimensional cell aggregate.

In the wall of the support, the bottom surface is also rough as in the surface of the upper surface of the support, and preferably has a root mean square average roughness Rq of 100 to 280μm and a linear density of 1.6 to 3.0 per 1 μm length.

When the well bottom surface also has the surface state as described above, it is easy to form cell aggregates in a space in the well because cells maintain a spherical shape easily.

When the root mean square average roughness Rq and the linear density are out of the ranges, the cell are easily maintained in a spherical shape and it is easy to form cell aggregates in a space in the well.

The well of the support, the bottom surface, and the side wall portion also preferably have the same root mean square average roughness Rq and linear density as those of the upper surface of the support, which are in each numerical range.

The cell culture support preferably have a patterned arrangement with a distance of 80 to 700 μm from a central point of the well, which is adjacent to the upper surface with a predetermined surface roughness.

When the distance from the central point of the well is less than 80 μm, the distance between cell aggregates formed becomes so close that it is difficult to supply oxygen or nourishment in a medium to cells. When the distance from the central point of the well is more than 700 μm, it is difficult for circular cells to migrate to the well.

In addition, it can be ensured that cells are put to the well by maintaining a distance of the well.

In order to make sure that a predetermined number of cells are seeded on the support, a wall higher than the upper surface at the outer perimeter of the support may be also formed.

In addition, a material for the cell culture support is preferably sintered ceramics.

The upper surface of the cell culture support may simply have the surface state as described above only with a concave-convex structure that ceramics particles form by constructing a cell culture support of a ceramics sintered body.

In addition, the sintered ceramics have pores between ceramics particles adjacent to each other, and these pores allows nourishment or inducing factors to permeate into the well from the bottom surface (rear surface) of the cell culture support by the capillary action.

The porosity of e sintered ceramics preferably from 10 to 50%, considering that permeation of the nourishment or inducing factors is secured and the strength of the support is mated.

The sintered ceramics preferably have an average pore size of 0.15 to 0 45 μm.

When the sintered ceramics have an average pore size in the above range, effects of the sintered ceramics are apparent.

The average pore size may be measured by the mammy intrusion porosimetry using a mercury porosimeter.

As described above, the cells recognize the unevenness of ceramics particles which contact with each other to change their shapes, and the sintered ceramics are affected by the surface state or damages when the surface of the sintered ceramics is processed. Thus, the surface of the support may be maintained in the surface state as it is after sintering the ceramics, that is, in the state when the process is not performed.

Furthermore, in order to form a cell aggregate on the surface of the ceramics, the secondary particles of the ceramics particles contacting cells preferably has an average particle size of 0.6 to 1.2 μm.

In the present invention, the average particle size of the secondary particles is obtained by suspending ceramics raw materials in pure water, subjecting the materials to sonication for 10 minutes, and using an ELSZ-2 apparatus from Otsuka Electronics Co., Ltd. to calculate the average value of the particle size distributions (laser Doppler method).

The surface roughness, average pore size, and average particle size of the support formed of the sintered ceramics may be appropriately controlled by adjusting the pre-sintering of ceramics raw material powder, the sintering temperature of the molded material and the like during the manufacture of the sintered body. For stable sintering, a stabilizer and the like may be added, if necessary.

As a material for the ceramics, zirconia, titania, alumina, or hydroxyapatite, which are excellent in bio-affinity and biocompatibility and appropriate as a foothold of cells, may be used. Among them, zirconia is preferably wed to form cell aggregates of mesenchymal stem cells efficiently.

When the support is manufactured by using zirconia, one or more of yttria, magnesium oxide, calcium oxide or serine oxide is preferably included as a stabilizer for zirconia in an amount of 3 to 15% by weight.

These stabilizers may be added to suppress the phase transition of zirconia and perform a sintering stably, and thus a support having the surface roughness as described above may be appropriately obtained.

For example, yttria may be added as a stabilizer to a zirconia raw material powder with an average particle size of 0.8 μm and sintered at 1,05° C. to 1,150° C. to manufacture a cell culture support having an appropriate surface roughness.

In addition, the well bottom surface preferably has a curved shape or a semicircular shape with the central portion depressed.

Through this shape, a plurality of cells permeated to the well may be aggregated, and thus cell aggregates may be formed easily.

In addition, the cell culture method according to the present invention is performed by using the support, and comprises:

disposing an upper surface of the support upwardly in it conger;

supplying a first culture medium to the container to permeate the first culture medium by the capillary action to the well opening of the support;

adding a second culture medium comprising undifferentiated mesenchymal stem cells dropwise to the upper surface of the support to culture mesenchymal stem cells;

supplying the fast culture medium to the container to immerse the support as a whole iii the first culture medium and to aggregate the mesenchymal stem cells in the well;

discharging the first culture medium and the second culture medium except for the mesenchymal stem cells out of the container;

supplying a third cult=medium for inducing differentiation of the mesenchymal stem cells which are aggregated into tissue cells such as hyaline chondrocytes, adipocytes and osteoblasts, to the container to immerse the support as a whole in the third culture medium to induce differentiation of mesenchymal stem cells into any tissue cell of hyaline chondrocytes, adipocytes and osteoblasts in the well.

The support according to the present invention as described above may be used and subjected to these steps to perform the formation of the aggregates of mesenchymal stem cells and the induction of the differentiation of the cell aggregates into tissue cells, such as hyaline chondrocytes, and adipocytes on the same support as it is without migrating the cells on the support, and thus the culture of tissue cells, such as hyaline chondrocytes, adipocytes and osteoblasts may be simply and efficiently performed.

In the cell culture method of the present invention, the number of mesenchymal stem cells in the second culture medium is preferably from $1\times10^4$ to $1\times10^6$ per 1 cm$^2$ of the support.

The cell culture support may be used to culture three-dimensional cell aggregates with a desired size more efficiently.

Hereinafter, the culture method will be described in detail in the order of steps.

First, the upper surface of the support is disposed upwardly in a container to supply a first culture medium to a gap between the container and the support. Subsequently, the culture medium is permeated to the well opening of the support by the capillary action.

The first culture medium may be supplied as described above to permeate the culture medium to the support through pores in the support from the bottom surface (rear surface) of the support by the capillary action without directly supplying the culture medium to the upper surface of the support, and thus the culture medium may be spread into every part of a plurality of wells without including bubbles which may be an inhibitory factor to culturing in the culture medium.

The type of the first culture medium is not particularly limited. However, for example, MEM, α-MEM, DMEM, Eagle's medium, and the like may be used for culturing mesenchymal stem cells. Materials which are necessary to maintain cells, such as FBS (bovine serum) and glutamic acid, may be added to the medium.

In addition, when mesenchymal stem cells are used as a tool far cell therapy, a commercially available serum-free medium is preferably used.

Subsequently, a second culture medium including undifferentiated mesenchymal stem cells is added dropwise to an upper surface of the support to seed mesenchymal stem cells on the support.

In this way, mesenchymal stem cells which are suspended in the culture medium may be added dropwise to an upper surface of the support to seed mesenchymal stem cells, and thus the cell aggregation may be achieved smoothly in the well because mesenchymal stem cells may be precipitated on the upper surface of the support without any load. The type of the medium used here is the same as that of the first culture medium.

The number of mesenchymal stem cells to be seeded on the support is preferably from $1\times10^4$ to $1\times10^6$ per 1 cm of the support.

Mesenchymal stem cells may be seeded at the density to culture three-dimensional cell aggregates with a desired size more efficiently by using the cell culture support.

Subsequently, the fast culture medium is further supplied to the container to immerse the entire support in the first culture medium and perform the aggregation of mesenchymal stem cells in the cell.

In the seeding step by adding the second culture medium dropwise, cells are attached to every part of the support surface in and out of the well. However, in the present step, the entire support is immersed in the first culture medium and may be allowed to stand for 48 hours or more, and thus cells attached to the upper surface of the support out of the well migrate to the well without being separated from the support to form aggregates in the well.

Furthermore, the first culture medium and the second culture medium except for the mesenchymal stem cells are discharged and a third culture medium is supplied to the container to immerse the entire support in the third culture medium, and induce the differentiation of mesenchymal stem cells which form a gates in the well into tissue cells, such as hyaline chondrocytes, adipocytes and osteoblasts.

In this way, a new culture medium may be supplied to the support which is used for culturing mesenchymal stem cells as it is, to induce the differentiation of mesenchymal stem cells into tissue cells, such as hyaline chondrocytes, adipocytes and osteoblasts in the well.

The third culture medium is a medium for inducing the differentiation of aggregated mesenchymal stun cells into tissue cells, such as hyaline chondrocytes, adipocytes and osteoblasts, and DMEM may be used as a basic medium and appropriately modified. Furthermore, TGFβ, BMP, and the like may be added, and additives, such as ascorbic acid, praline, dexamethasone, insulin, transferrin and selenious acid may be added.

Any type of TGFβ may be used as long as it belongs to the TGFβ family, and TGFβ-3 is preferably used. Instead, a low molecular weight compound which shows the same action as TGFβ may be used. TGFβ to be added is preferably from 1 to 50 ng/ml, and more preferably 10 ng/ml.

As for BMP, BMP2, BMP4, BMP6, and the like are used and BMP6 is preferably used for example. Also, a low molecular weight compound may be used. BMP to be added is preferably from 100 to 500 ng/ml, and more preferably 200 ng/ml.

In addition, ascorbic acid (preferably ascorbic acid 2-phosphoric acid) to be added is preferably from 10 to 100 μg/ml, and more preferably 50 μg/ml.

In addition, proline to be added is preferably from 10 to 100 μg/ml, and more preferably 40 μg/ml.

In addition, dexamethasone to be added is preferably from free 10 to 500 nM, and prefer 100 nM.

In addition, insulin, transferrin, and selenous acid may be added to have a suitable limit of a commercially available ITS solution.

Differentiation-inducing medium which induce mesenchymal stem cells cartilage, fat and osteoblasts are commercially available, and these may be used as well.

EXAMPLE

Hereinafter, the present invention will described in detail with reference to Examples. However, the present invention is not limited to the following Examples.

Test Example 1-1

Cell Culture Support Formed of a Zirconia Raw Material unsintered powder

A zirconia raw material powder with an average particle size of 0.5 to 0.9 μm was molded by using a special cast with a plurality of patterned convex shapes, whose size is slightly smaller dun the size of a desired well shape, was used to mold a zirconia cell culture support (diameter 15 mm) with wells having an opening size of 100 μm and a depth of 100 μm arranged, and allowed to stand at room temperature, and then the molded material was removed from the cast, dried at a predetermined temperature for 24 hours, and sintered at 1,050° C., 1,150° C., 1,250° C., 1,350° C., and 1,500° C. for 2 hours, respectively, to prepare a support.

The average opening size of wells in each support manufactured was 82 μm, 78 μm, 64 μm, 60 μm, and 55 μm, respectively.

An average value of opening sizes calculated by a calculation method of the opening size, including the step of randomly drawing eight diameter lines passing through the central point of a well. The result was each applied to twenty wells to calculate an average value of opening sizes in each well.

An opening size of the well was measured by using a microscope (VHX-1000: Keyence).

Figure 1:
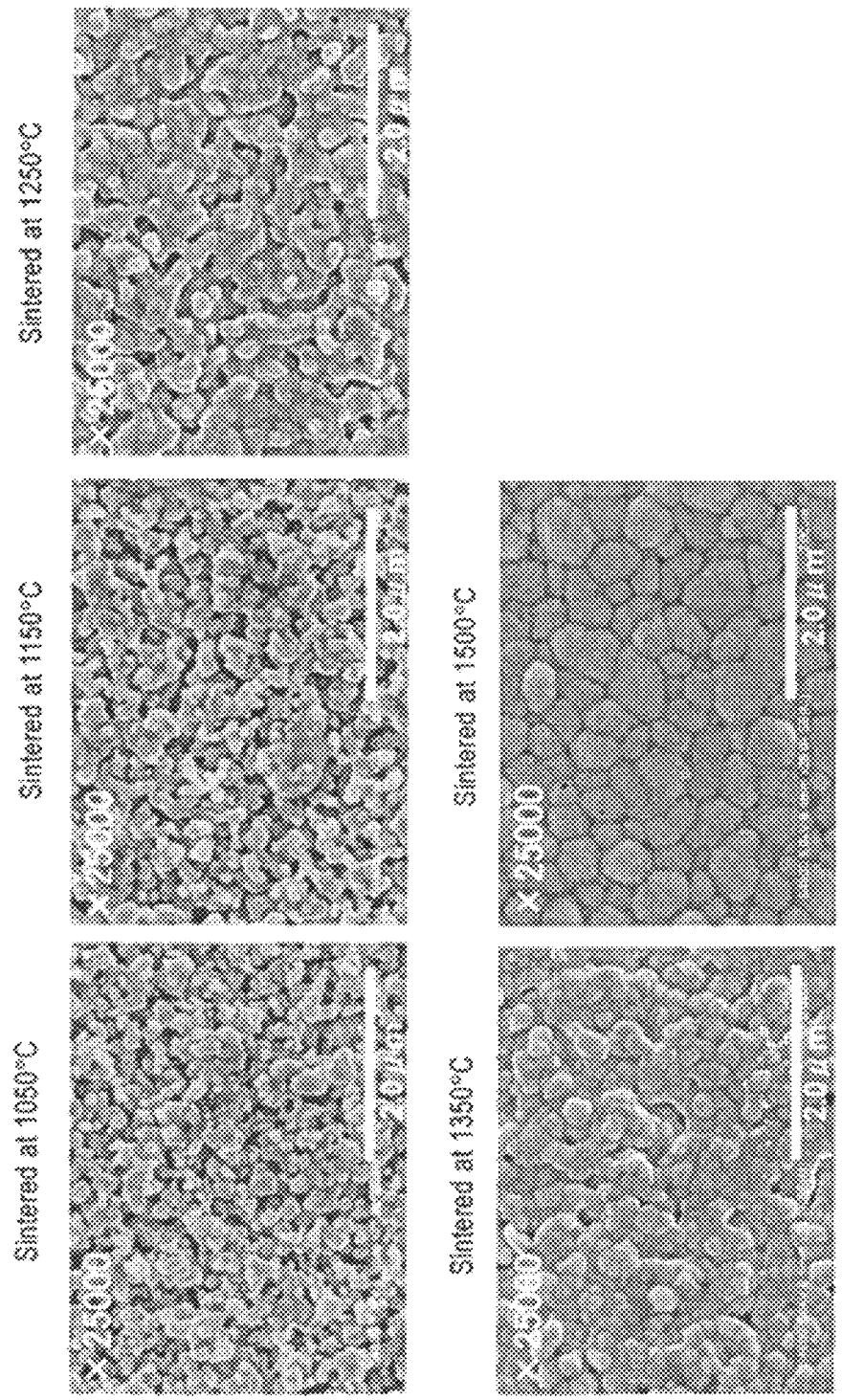
FIG. 1 is a scanning electron microscopy (SEM) photo (x25,000) of the surface skeleton of a zirconia cell culture support (sintered at 1,050° C. to 1,500° C.) manufactured by using a zirconia raw material powder (unsintered powder) according to Test Example 1-1.
Figure 2:
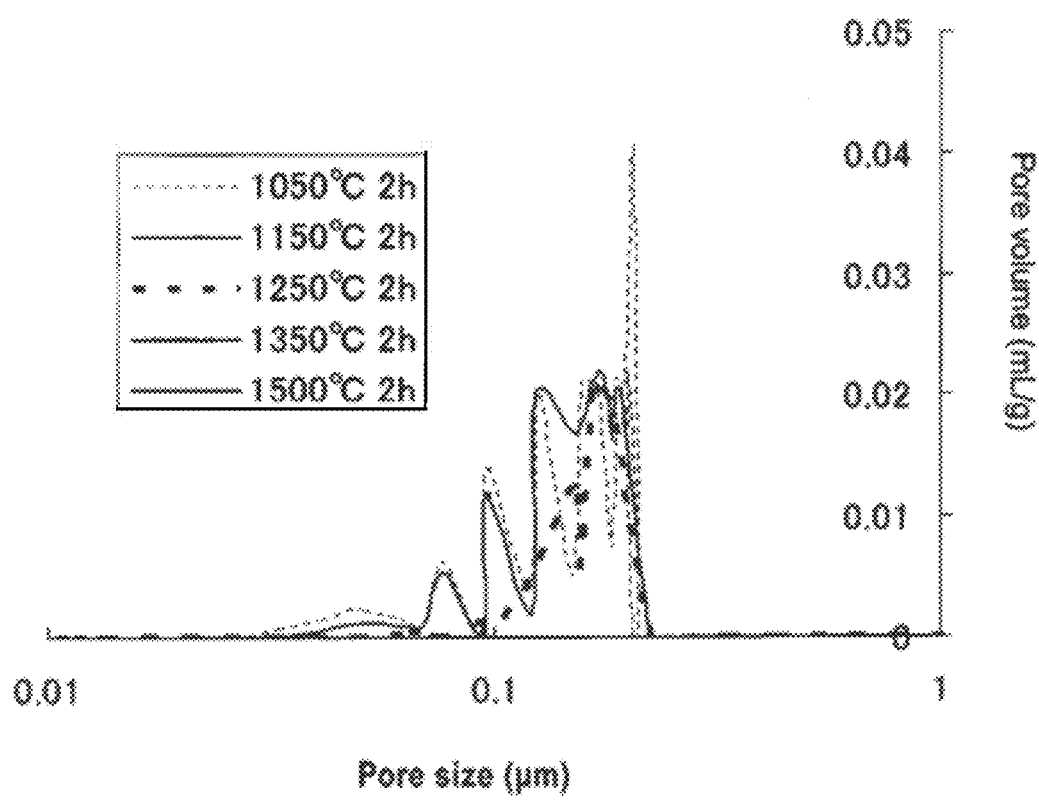
FIG. 2 is a graph showing a pore size distribution of a zirconia cell culture support (sintered at 1,050° C. to 1,500° C.) manufactured by using a zirconia raw material powder (unsintered powder) according to Test Example 1-1, measured by the mercury intrusion porosimetry.

For a zirconia cell culture support sintered at each temperature, FIG. 1 illustrates a scanning electron microscopy (SEM) photo of the surface skeleton and FIG. 2 illustrates a pore size distribution, measured by mercury intrusion porosimetry.

The average particle size was obtained by suspending ceramics raw materials in pure water, subjecting the materials to sonication for 10 min, and using an ELSZ-2 apparatus from Otsuka Electronics Co, Ltd. to calculate the average value of particle size distributions (laser Doppler method).

As shown from the SEM to shown FIG. 1, it is acknowledged that particles were sintered and densified as the sintering temperature increased.

In addition, as shown in the graph in FIG. 2, it is identified that the densificaton was proceeded and micro-pores became smaller as the sintering temperature increased. The average pore sizes of ceramics sintered at 1,050° C., 1,150° C., and 1,250° C. were 0.17 μm, 0.15 μm, and 0.17 μm, respectively. Micro-pores were not detected from ceramics bodies sintered at 1,350° C. and 1,500° C.

In addition, each support manufactured above was sterilized and placed in a 24 well plates. An immortalized human mesenchymal stem cell (hMSC) was seeded on this at the density of $1 \times 10^4$ cells, and cultured at 37° C. under 5% CO2 in a DMEM including 10% FBS (bovine serum).

Figure 3:
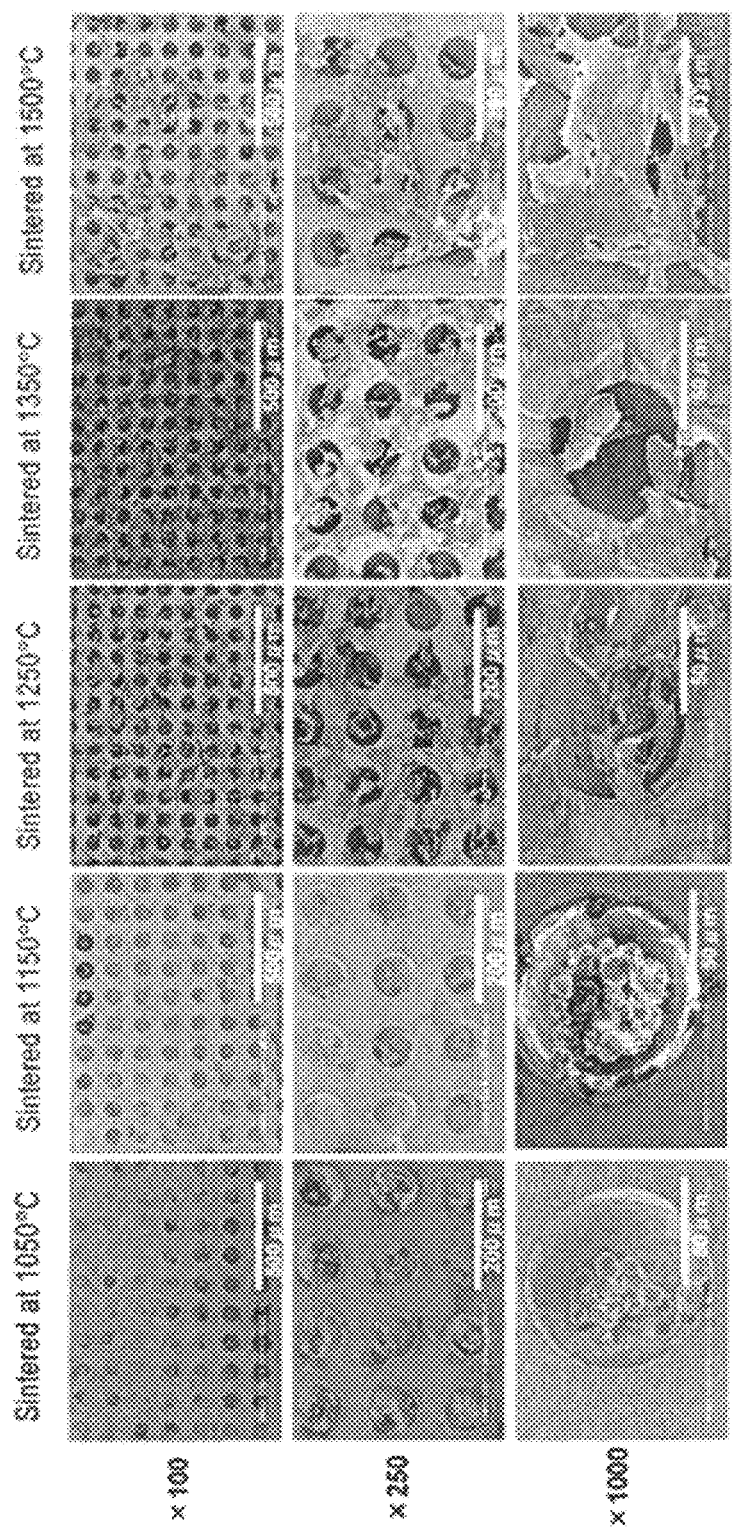
FIG. 3 is a group of SEM photos (x100, x250, and x1,000) of human mesenchymal stem cells (hMSCs) cultured on a zirconia cell culture support (sintered at 1,050° C. to 1,500° C.) with wells having an opening size of 100 μm arranged according to Test Example 1-1.

FIG. 3 illustrates a group of SEM days of seeding.

As shown from a group of SEM photos shown in FIG. 3, when supports sintered at 1,050° C. and 1,150° C. were used, it is acknowledged that hMSCs were gathered in the well to form circular cell aggregates, and cells were not adhered to the upper surface (out of the well) of the support. When a support sintered at 1,250° C. was used, squamous cells were adhered to the upper surface of the support even though aggregates of cells were formed in the well. When supports sintered at 1,350° C. and 1,500° C. were used, squamous cells were adhered in and out of the well.

Test Example 1-2

Cell Culture Support Formed of a Zirconia Raw Material Powder Pre-sintered at 1,150° C.

A zirconia raw material powder used in Test Example 1-1 was pre-sintered at 1,150° C. to obtain secondary particles with an average particle size of 0.75 to 1.2 μm. These secondary particles were used to mold a zirconia cell culture support (diameter 15 mm) with wells having an opening size of 100 μm and a depth of 100 μm arranged in the same manner as in Test Example 1-1, and thus the support was altered at 1,050° C., 1,150° C., 1,250° C., 1,350° C., and 1,500° C., respectively for 2 hours to manufacture the support.

The average opening sizes of wells in each support manufactured were 90 μm, 85 μm, 75 μm, 65 μm, and 55 μm, respectively. The calculation method of the opening size is as described above.

Figure 4:
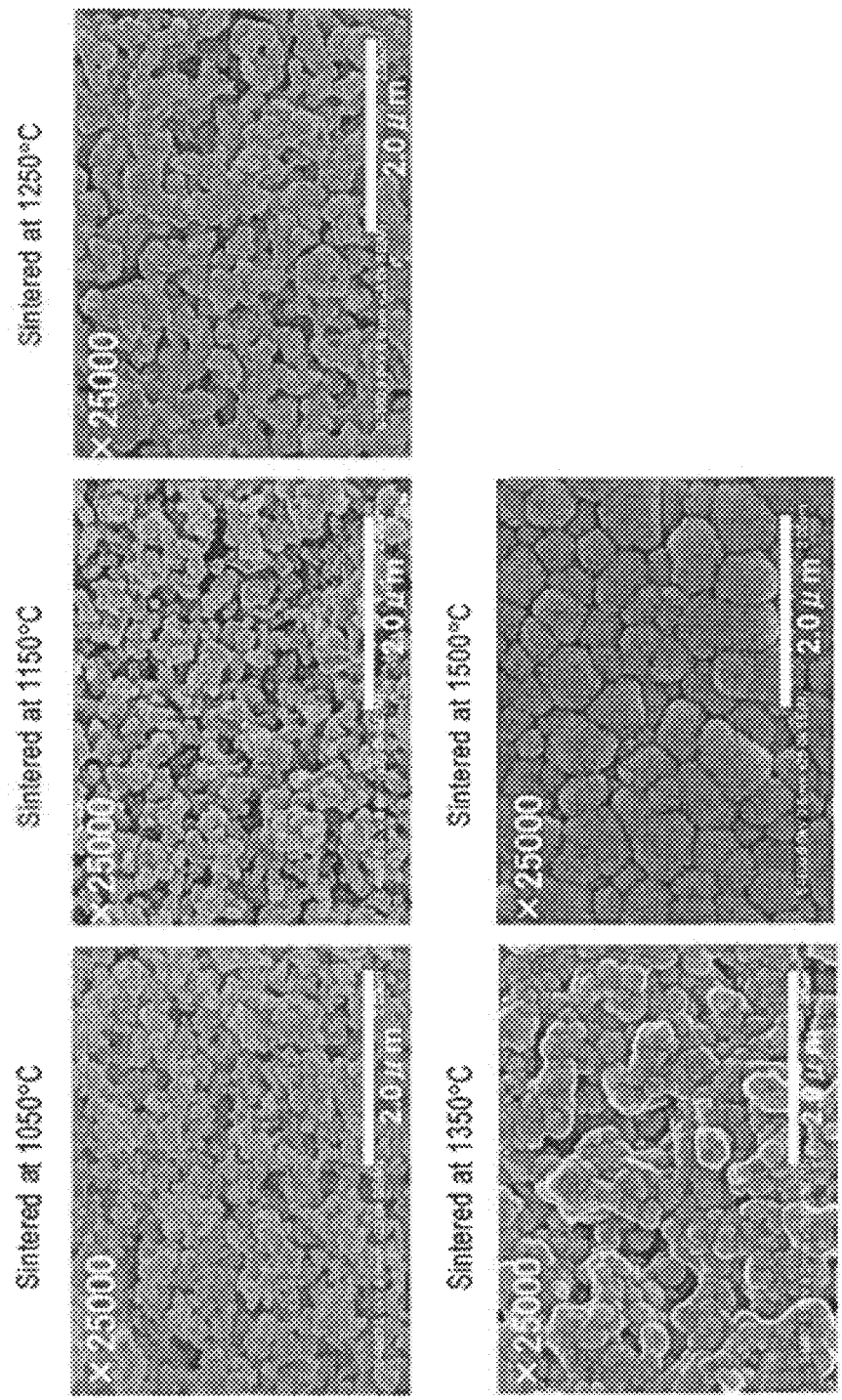
FIG. 4 is an SEM photo (x25,000) of the surface skeleton of a zirconia cell culture support (sintered at 1,050° C. to 1,500°

For zirconia cell culture supports sintered at each temperature, FIG. 4 illustrates an SEM photo of the surface skeleton and FIG. 5 illustrates a pore size distribution, measured by mercury intrusion porosimetry.

As shown from the SEM photo shown in FIG. 4, the support manufactured by using secondary particles pre-sintered at 1,150° C. was formed of larger particles than the support manufactured by using an unsintered mw material powder (Test Example 1-1), and it is acknowledged that particles were sintered and densified as the sintering temperature it creased.

In addition, as shown in the graph in FIG. 5, it is acknowledged that the support sintered at the temperature in Test Example 1-1 had somewhat bigger micro-pores. The average pore sizes of ceramics sintered at 1050° C., 1,150° C., and 1,250° C. were 0.25 μm, 0.22 μm, and 0.20 μm, respectively. Micro-pores were not detected from ceramics bodies sintered at 1,350° C. and 1,500° C.

Each support manufactured above was also used to culture hMSCs in the same manner as in Test Example 1-1.

FIG. 6 illustrates a group of SEM photos after 3 days of seeding.

As shown dam the SEM photos shown in FIG. 6, when supports sintered at 1,454° C., 1,150° C., and 1,250° C. were used, it is acknowledged that hMSCs were gathered in the well to form circular cell aggregates, and cells were not adhered to the upper surface (out of the well) of the support. When supports sintered at 1,350° C. and 1,500° C. were used, squamous cells were adhered in and out of the well.

Test Example 1-3

Cell Culture Support Formed of a Zirconia Raw Material Powder Pre-sintered at 1,250° C.

A zirconia raw material powder used in Test Example 1-1 was pre-sintered at 1,250° C. to obtain secondary particles with an average particle size of 0.8 to 1.2 μm. These secondary particles were used to mold a zirconia cell culture support (diameter 15 mm) with wells having an opening size of 100 μm and a depth of 100 μm arranged in the same manner as in Test Example 1-1, and thus the support was sintered at 1,050° C., 1,150° C., 1,250° C., 1,350° C., and 1,500° C., respectively, for 2 hours to manufacture the support.

The average opening sizes of wells in each support manufactured were 92 μm, 88 μm, 77 μm, 65 μm, and 57 μm, respectively. The calculation method of the opening size is as described above.

For zirconia cell culture supports sintered at each temperature, FIG. 7 illustrates an SEM photo of the surface skeleton and FIG. 8 illustrates a pore size distribution, measured by the mercury intrusion porosimetry.

As shown m the SEM photo shown in FIG. 7, the support manufactured by using a powder pre-sintered at 1,250° C. was formed of larger particles than the support manufactured by using an unsintered raw material powder or a powder pre-sintered at 1,150° C. (Test Examples 1-1 and 1-2), and it is acknowledged that particles were sintered and densified as the sintering temperature increased.

In addition, as shown in the graph in FIG. 8, it is acknowledged that the supports sintered at the temperature in Test Examples 1-1 and 1-2 had somewhat bigger micro-pores. The average pore sizes of ceramics sintered at 1,050° C., 1,150° C., and 1,250° C. were 0.45 μm, 0.34 μm, and 0.42 μm, respectively. Micro-pores were not detected from ceramics bodies sintered at 1,350° C. and 1,500° C.

Each support manufactured above was also used to culture hMSCs in the same manner as in Test Example 1-1.

FIG. 9 illustrates a group of SEM photos alter 3 days of seeding.

As shown from the SEM photos shown in FIG. 9, when supports sintered at 1,050° C., 1,150° C., and 1,2500° C. were used, it is acknowledged that hMSCs were gathered in the well to form circular cell aggregates, and cells were not adhered to the upper surface (out of the well) of the support. When supports sintered at 1,350° C. and 1,500° C. were used, squamous cells were adhered in and out of the well.

Test Example 1-4

Cell Culture Support Formed of a Zirconia Raw Material Powder Pre-sintered at 1,350° C.

A zirconia raw material powder used in Test Example 1-1 was pre-sintered at 1,350° C. to obtain secondary particles with an average particle size of 1.0 to 2.5 μm. These secondary particles were used to mold a zirconia cell culture support (diameter 15 mm) with wells having an opening size of 100 μm and a depth of 100 μm arranged in the same manner as in Test Example 1-1, and thus the support was sintered at 1,050° C., 1,150° C., 1,250° C., 1,350° C., and 500° C., respectively for 2 hours to manufacture the support.

The average opening sizes of wells in each support manufactured were 85 μm, 82 μm, 75 μm, 67 μm, and 58 μm, respectively. The calculation method of the opening size is as described above.

For zirconia cell culture supports sintered at each temperature, FIG. 10 illustrates au SEM photo of the surface, skeleton and FIG. 11 illustrates a pore size distribution, measured by mercury intrusion porosimetry.

As shown from the SEM photo shown in FIG. 10, the support manufactured by using secondary particles pre-sintered at 1,350° C. was formed of larger panicles than the support manufactured by using an unsintered raw material powder, secondary particles pre-sintered at 1,150° C., or secondary particles pre-sintered at 1,250° C. (Test Examples 1-1, 1-2, and 1-3), and it is acknowledged that particles were sintered and densified as the sintering temperature increased.

In addition, as shown in the graph in FIG. 11, it is acknowledged that the supports sintered at the temperature in Test Examples 1-1 to 1-3 bad somewhat bigger micro-pores. The average pore sizes of ceramics sintered at 1,050° C., 1,150° C., and 1,250° C. were 0.64 μm, 0.91 μm, and 0.72 μm, respectively. Micro-pores were not detected from ceramics bodies sintered at 1,350° C. and 1,500° C.

Each support manufactured above was also used to culture hMSCs in the same manner as in Test Example 1-1.

FIG. 12 illustrates a group of SEM photos after 3 days of seeding.

As shown from the SEM photos shown in FIG. 12, squamous cells were adhered in and out of the well at all the sintering temperatures.

In addition, for the shapes of cells cultured on each support manufactured in Test Examples 1-1 to 1-4, Table 1 shows a relationship with the root mean square average roughness Rq of the upper surface in each support and Table 2 shows a relationship with the linear density of the upper surface in each support.

The root mean square average roughness Rq is measured by JIS B 0601.

The linear density is also measured with a scale of 0.8 μm and a scan size of 10×10 μm by atomic force microscopy (AFM).

TABLE 1

| Pre-sintering temperature of raw material | Particle size (μm) | 1,050° C. | 1,150° C. | 1,250° C. | 1,350° C. | 1,500° C. |
|---|---|---|---|---|---|---|
| n/a | 0.6 to 0.9 | ○ 133.48 nm | ○ 101.35 nm | Δ 77.93 nm | X 69.83 nm | X 64.19 nm |
| 1,150° C. | 0.75 to 1.2 | ○ 173.45 nm | ○ 155.348 nm | ○ 136.03 nm | X 70.12 nm | X 63.59 nm |

TABLE 1-continued

| Pre-sintering temperature of raw material | Particle size (μm) | 1,050° C. | 1,150° C. | 1,250° C. | 1,350° C. | 1,500° C. |
|---|---|---|---|---|---|---|
| 1,250° C. | 0.8 to 1.2 | ○ 272.61 nm | ○ 252.24 nm | ○ 230.44 nm | X 68.12 nm | X 62.62 nm |
| 1,350° C. | 1.0 to 2.5 | X 232.16 nm | X 229.72 nm | X 197.48 nm | X 75.87 nm | X 59.47 nm |

○: Circular aggregate of cells, Δ: Circular aggregate and planarized shape of cells, X: Planarized shape of cells

TABLE 2

| Pre-sintering temperature of raw material | Particle size (μm) | 1,050° C. | 1,150° C. | 1,250° C. | 1,350° C. | 1,500° C. |
|---|---|---|---|---|---|---|
| n/a | 0.6 to 0.9 | ○ 2.75 | ○ 2.8 | Δ 2.25 | X 1.55 | X 1.15 |
| 1,150° C. | 0.75 to 1.2 | ○ 2.45 | ○ 2.3 | ○ 2.4 | X 1.5 | X 1.2 |
| 1,250° C. | 0.8 to 1.2 | ○ 1.6 | ○ 1.8 | ○ 2.25 | X 1.65 | X 1.25 |
| 1,350° C. | 1.0 to 2.5 | X 1.35 | X 1.4 | X 1.45 | X 1.4 | X 1.15 |

○: Circular aggregate of cells, Δ: Circular aggregate and planarized shape of cells, X: Planarized shape of cells From results shown in Tablas 1 and 2, when the upper surface in each support has a root mean square average roughness Rq of 100 to 280 nm and a linear density of 1.6 to 3.0 per 1 μm length, it is acknowledged that hMSCs tend to form aggregates.

In addition to what is described above, when the well has a root mean square average roughness Rq of 100 to 280 μm in at least bottom surface and a linear density of 1.6 to 3.0 per 1 μm length, it is acknowledged that hMSCs tend to form more aggregates.

Example 1

Culture of hMSC

A zirconia cell culture support was prepared by sintering zirconia-based powder with average pore size of 0.6 to 0.9 μm at 1,150° C. In the zirconia cell support lined with wells with an opening size and depth of 78 μm, 175 μm, and 510 μm, hMSCs having the cell number of $0.5 \times 10^4$, $1 \times 10^4$, $2.5 \times 10^4$, and $5 \times 10^4$ were seeded and cultured as described in Experiment 1-1.

FIG. 13 illustrates SEM photos ager 7 days of seeding.

As shown from the SEM photo in FIG. 13, it has been confirmed that cell tends to be aggregated in the well, when the well opening size was 78 μm, and the number of hMSC seeded was greater than $1 \times 10^4$.

In addition, when the well opening size was bigger than 175 μm, it has been confirmed that cell tends to be easily aggregated when the number of cells seeded was greater than $5 \times 10^4$.

The hMSCs were seeded and cultured in following cell culture supports; zirconia cell culture support lined with wells with opening size and depth of 70 μm, 175 μm, and 550 μm prepared from zirconia-based powder with average pore sizes of 0.6 to 0.9 μm and sintered at 1,050° C.; the zirconia cell culture support lined with wells with opening size and depth of 70 μm, 175 μm, and 550 μm prepared with the zirconia-based powder with average pore sizes of 0.75 to 1.2 μm pre-sintered at 1,150° C. and further sintered at 1,050° C. 1,15° C., and 1,25° C.; the zirconia cell culture support lined with wells with opening size and depth of 70 μm, 175 μm, and 550 μm prepared with the zirconia powder with average pore sizes of 0.8 to 1.2 μm presintered at 1,250° C. and further sintered at 1,050° C. 1,150° C., and 1,250° C. As a result, it has been confirmed that cell tends to be aggregated in the wells of each of the cell culturing support.

Comparative Example 1

Culture of HepG2

A zirconia cell culture support lined with wells with opening size and depth of 175 μm was manufactured using zirconia powder having the average pore sizes of 0.6 to 0.9 μm. The surface of the cell culture support had root mean square roughness Rq of 103.22 nm, and a linear density of 2.71.

The support was sterilized and inserted in the 24 well plates. Human liver cancer derived cells (HepG2) were seeded at the density of $5 \times 10^4$ cells in DMEM containing 10% FBS, and cultured at 37° C. under 5% $CO_2$.

FIG. 14 illustrates SEM photos after 7 days of seeding.

As shown from SEM pictures represented in FIG. 14, in the cell culture support of the present invention, the HepG2 did not form aggregates inside the well (concave), but found to be attached on the convex (upper surface).

Comparative Example 2

General Method of Culturing hmscs on Petri Dishes

Immortalized hMSCs at the density of $3 \times 10^5$ cells were seeded on a gelatin coded 10 cm petri dish in a DMEM, containing 10% FBS and cultured at 37° C. under 5% $CO_2$.

FIG. 15 illustrates microscopic photos of the petri dish after 3 days of seeding.

As shown in the microscopic photos in FIG. 15, the hMSCs did not form cell aggregates on the petri dish surface but was attached in the form of flat layer.

Comparative Example 3

Culture of hMSCs on a Zirconia Flat Surface

A zirconia flat surface was manufactured according to Comparative example 1, except for the mold being a flat surface rather than a concave-convex shape. The surface of the cell culture support had root moan square roughness Rq of 100.8 nm and a linear density of 2.01.

The flat surface was sterilized and inserted in the 24 well plates. Human liver cancer derived cells (HepG2) were seeded at the density of $1 \times 10^4$ cells in DMEM containing 10% FBS, and cultured at 37° C. under 5% $CO_2$.

FIG. 16 illustrates SEM photos after 3 days of seeding.

According to the SEM photos shown in FIG. 16, when the hMSCs were cultured with zirconia flat surface, the shape of the each cells turned into a sphere but did not form cell aggregates.

Therefore, it is suggested that a well structure is required for hMSC aggregating and in addition, the well surface should be a concave-convex form instead of a flat surface.

Example 2

Differentiation-induction of hMSC into Chondrocytes

By using zirconia powder with average pore sues of 0.6 to 0.9 μm, a zirconia cell culture support lined with wells with opening size and depth of 100 μm (diameter 15 mm) were molded, and than sintered for 2 hours at 1,150° C. to make a support with an opening size and depth of 70 μm.

This support was sterilized and inserted in the 24 well plates. Immortalized hMSC were seeded at the density of $5 \times 10^4$ cells in DMEM containing 10% PBS, and cultured at 37° C. under 5% $CO_2$.

Three days after seeding, differentiation was induced by replacing the culture medium with DMEM (chondrogenic differentiation-inducing medium) containing 10 ng/ml. of TGFβ-3, 100 nM of DEC, 50 μg/ml of ascorbic acid, 40 μg/ml of proline, ITS and pyruvic acid for 3 weeks. The culture medium was replaced every 4 days.

One, two, three and four weeks after differentiation-induction, differentiation-inducing medium was removed from each support, washed with PBS, then, the RNA was extracted immediately. The mRNA was extracted and purified by using RNAisoPlus (Takara Co.) according to manufacturer's protocols.

The extracted RNA was reverse transcribed using RNA PCR kit (Takara Co.), than the expression of chondrocyte differentiation markers, CD29, CD44, CD105, Type X collagen, Type II collagen, COMP, Aggrecan, SOX9, Lunx2, and ChMI were identified by PCR.

These chondrocyte differentiation markers are shown in FIG. 17. For comparison, normal cell markers for cartilage tissue and hyaline cartilage derived by inducing the differentiation of hMSC aggregates were shown as well.

Here, markers represented as + for expression, and as – for non-expression, include: in hMSC, CD29+, CD44+, CD105+, Type X collagen–, Type II collagen–, COMP–, Aggrecan–, Sox9–, Lunx2–, ChMI–; in human derived chondrocyte (hyaline chondrocytes) CD29+, CD44+, CD105–, Type X collagen–, Type II collagen+, COMP+, Aggrecan+, Sox9+, Lunx2–, ChMI–; in mature-hypertrophic chondrocytes, Type X collagen+, Type II collagen–, COMP–, Aggrecan–, Sox9–, Lunx2+, arid ChMI+.

According to the result shown in FIG. 17, when the hMSC aggregate size was limited through the cell culture support well and was induced to differentiate, there were expressions of CD29, CD44, Type E collagen, COMP, aggrecan, and Sox9. The expression level increased when the induction time was longer. in addition, the expression of Type X collagen, Lunx2, ChMI was not detected, but gene expression was similar to those of hyaline chondrocytes sampled from human body.

The hMSCs were seeded and incubated in following cell culture supports; zirconia cell culture support lined with wells with opening size and depth of 175 μm and 550 μm which was prepared with zirconia powder with average pore sizes of 006 to 0.9 μm and sintered at 1,050° C.; the zirconia cell culture support lined with wells with opening size and depth of 175 and 550 μm which was prepared with the zirconia powder with average pore sizes of 0.75 to 1.2 μm, presintered at 1,150° C. and further sintered at 1,050° C., 1,150° C. and 1,250° C.; the zirconia cell culture support lined with wells with opening size and depth of 175 μm and 550 μm which was prepared with the zirconia powder with average pore sizes of 0.8 to 12 μm, presintered at 1,250° C. and further sintered at 1,050° C., 1,150° C., and 1,250° C. As confirmed by chondrocyte differentiation markers, these cultured cells showed similar gene expression pattern as hyaline chondrocytes from human body.

Comparative Example 4

Differentiation-induction of hMSC into Hyaline chondrocyte using a pellet method $2.5 \times 10^5$ of immobilized hMSCs suspended in 5 ml of DMEM, the suspension was poured into a 15 ml tube, and the cell pellet was collected from the bottom of the tube by centrifugation. DMEM medium was aspirated, then replaced with DMEM (chondrogenic differentiation-inducing medium) containing 10 ng/ml of TGFβ, 100 nM of DEX, 50 μg/ml of ascorbic acid, 40 μg/ml of proline, ITS, and pyruvic acid end hMSCs induced for 3 weeks. The culture medium was replaced every 14 days.

After differentiation-induction for 1, 2 and 3 weeks later, the differentiation-inducing medium was removed from each support, washed with PBS, then RNA was extracted immediately. Extraction of RNA and PCR detection of chondrocyte differentiation marker was performed as described in Example 2.

These chondrocyte differentiation marker results are shown in FIG. 17 in addition to Example 2.

Based on the result shown in FIG. 17, when the hMSC aggregate formed by pellet method was induced for differentiation, hyaline chondrocyte specific genes CD29, CD44, Type II collagen, COMP, aggrecan and Sox9 were expressed, and Type X collagen was also expressed.

This result shows that the chondrocytes collected contained not only the target hyaline chondrocytes but also mature hypertrophic chondrocyte; therefore suggesting that these chondrocytes were not a homogeneously differentiated cartilage tissue.

Example 3

Differentiation Induction of hMSC with Different Well Opening Sizes into Hyaline Chondrocyte.

Using zirconia powder with average pore sizes of 0.6 to 0.9 μm, each cell culture support (diameter 15 mm) lined with wells with opening size and depth of 100 μm, 200 μm, 400 μm, 680 μm were molded, then sintered for 2 hours at 1,150° C. to produce support with opening size and depth of 78 μm, 175 μm, 350 μm, and 510 μm.

Using each of the supports prepared above, hMSC was cultured and hMSC was induced according to Example 2.

Three weeks after differentiation-induction, the differentiation-inducing medium was removed from each support, washed with PBS, then RNA was extracted immediately. The RNA was extracted by using RNAisoPlus (Takara) according to manufacturer's protocols.

The extracted RNA was reverse transcribed using RNA PCR kit (Takara Co.), then the expression of mesenchymal stem cell marker CD105, mature/hypertrophic chondrocytes marker Type X collagen, hyaline chondrocyte specific marker Type II collagen, was identified by PCR.

These markers are shown in FIG. 18. In addition, for comparison, cartilage tissue markers obtained by inducing the differentiation of hMSC cell aggregates formed by pellet method, were shown as well.

Based on tae result shown in FIG. 18, the cartilage tissue derived from hMSC aggregate formed by incubating in a cell support with the well opening sizes of 78 to 510 μm showed expression of Type II collagen, but not of Type X collagen and DC105. This result confirms that homogeneous hyaline chondrocytes has been induced.

However, the cartilage tissue obtained by pellet method showed expression of Type II collagen, Type X collagen and CD105, suggesting that this tissue consisted of mixtures of mesenchymal stem cells, hyaline chondrocytes and mature/hypertrophic chondrocytes.

In addition, hMSCs were seeded and incubated in following cell culture supports; zirconia cell culture support lined with wells with opening size and depth of 70 μm, 175 μm, 350 μm, and 510 μm prepared with zirconia powder with average pore sizes of 0.6 to 0.9 μm and sintered at 1,050° C.; the zirconia cell culture support lined with, wells with opening size and depth of 70 μm, 175 μm, 350 μm, and 510 μm prepared with the zirconia powder with average pore sizes of 0.75 to 1.2 μm, presintered at 1,150° C. and further sintered at 1,050 ° C., 1,150° C., and 1,250° C.; the zirconia cell culture support lined with wells with opening size and depth of 70 μm, 175 μm, 350 μm, and 510 μm prepared with the zirconia powder with average pore sizes of 0.8 to 1.2 μm, presintered at 1,250° C. and further sintered at 1,050° C., 1,150° C., and 1,250° C.

As confirmed by chondrocyte differentiation markers, these cultured cells showed similar gene expression pattern as hyaline chondrocytes from human body.

Example 4

Staining of Differentiation Weed Cartilage Tissue

According to Example 3, differentiation-inducing medium was removed from cell culture support (well opening size and depth is 510 μm), which was differentiation-induced for 3 weeks, washed with. PBS, and fixed with 4% paraform aldehyde (Wako Co.). The cells were then dehydrated with 70, 30, 90, and 100% ethanol, followed by immersion in xylene.

The cartilage tissue was recovered from the well of the supp by pipetteting then the tissue was paraffin embedded. The paraffin block was cut into 5 μm thickness sections using microtome (Leica Co.). The sections were attached to slide glass, deparffinized by immersing in following solutions, Xylene, 100, 90, 80, and 70% ethanol, and prepared for further staining.

After immersing the sections in 3% acetic acid, the sections were stained for 5 min with saphranine O or toluidine blue, which specifically stains the extracellular substrate glucosaminoglycan produced by the chondrocytes. The sections were dehydrated with alcohol and xylene, and then mounted with mounting solution.

The microscopic photos of saphranine O and toluidine blue stained tissues am presented in FIGS. 19 and 20, respectively. In addition, the images of cartilage tissue derived from the induction of the differentiation of hMSC aggregates formed by pellet method are shown as comparison.

According to the light microscopic images presented in FIGS. 19 and 20, the cartilage tissue derived from induction of the differentiation of hMSC aggregates was stained evenly to the central region by saphranine O (red-violet) and toluidine blue (blue-violet). This result confirms that the cartilage tissue in the present invention has formed externally and internally uniform chondrocyte tissue.

Similar results were confirmed while using zirconia cell culture supports with various opening size and depth produced by different sintering temperatures, as described in Examples 2 and 3.

Comparative Example 5

Staining of Differentiation-induced Cartilage Tissue by Pellet Method

According to Comparative Example 4, cell differentiation inducing medium was removed from tissue which was differentiation-induced for 3-weeks from hMSC aggregates that was by pellet method. Following the method described in Example 4, tissue was stained with saphranine O and toluidine blue.

The microscopic photos of saphranine O and toluidine blue stained tissues are shown in FIGS. 19 and 20, along with the result from Example 4.

According to the light microscopic images presented in FIGS. 19 and 20, the cartilage tissue derived from differentiation-induced hMSC aggregates formed by pellet method showed staining of only the peripheral region and not so much of the central region of the tissue. This result indicates that there was a difference in the distribution of external and internal chondrocyte differentiation, hence confirming an uneven cartilage tissue was formed.

Test Example 2

Culture of hMSC in Each Well Opening

Using zirconia raw material powder with average pore sizes of 0.6 to 0.9 μm, zirconia cell culture support (diameter 15 mm) lined with wells with opening size and depth of 30 μm, 70 μm, 540 μm, and 1410 μm molded and produced by sintering at 1,150° C. for 2 hours.

The support was sterilized and inserted in the 24 well plates. Immortalized hMSC were seeded at the density of $5\times10^4$ is DMEM containing 10% FBS, and incubated at 37° C. under 5% $CO_2$.

FIG. 21 illustrates SEM photos after 3 days of seeding.

Based on the SEM pictures from FIG. 21, cell culture supports with well opening size of 70 μm, 540 μm showed that cells were forming a cell aggregate only inside the well.

However, in the cell culture supports with well opening size of 30 μm, squamous cells were attached out of the well (upper surface of the support) and there were not enough cell aggregates formed. In addition, in the cell support with well opening size of 1410 μm, even though cells were collected inside the well, not enough cell aggregates formed in the well.

Comparative Example 6

Alumina Cell Culture Support

Alumina cell culture support (diameter 15 cm) lined with wells with opening size and depth of 100 μm was molded and produced by sintering at 1,000° C. for 2 hours, as described in Example 1, except for using alumina powder as the raw material and using spray dryer for secondary pore formation (identical alumina ceramics porous material described in Example 1 of Patent Document 1). The average opening size of 10 wells formed on the support surface after sintering was 80 μm. The SEM images of the surface structure of the Alumina cell culture support are shown in FIG. 22.

The surface of the cell culture support had root mean square roughness Rq of 47.40 nm, and the linear density of 5.01, as described by the method for measuring the carries in Test Examples 1-1 to 1-4.

The support was sterilized and inserted in the 24 well plates. Immortalized hMSCs were seeded at the density of $1 \times 10^4$ cells in DMEM containing 10% FBS, and in bat at 37° C. under 5% $CO_2$.

FIG. 23 illustrates SEM photos (x100, x200, and x1000) after 3 days of seeding.

As indicated by the images in FIG. 23, mesenchymal stem cells were attached flat on the concavo-convex surface, thus not forming the cell aggregate.

Example 5

Differentiation-induction of hMSC into Adipocytes

Using powdered zirconia with average particle sizes of 0.6 to 0.9 μm raw material, zirconia cell culture support lined with wells with opening size and depth of 100, 200, 400, 600 μm ware molded and sintered at 1,150° C. for 2 hours. Each zirconia cell culture support was reduced to wells with opening size and depth of 75, 175, 350, and 510 μm after sintering.

The supports were sterilized and inserted in the 24 well plates. Immortalized hMSC were seeded at the density of $1 \times 10^5$ (a well opening size of 75 μm), $2 \times 10^5$ (a well opening size of 175 μm), $3 \times 10^5$ (a well opening size of 350 μm), $4 \times 10^5$ cells (a well opening size of 510 μm) in DMEM containing 10% FBS, and incubated at 37° C. under 5% $CO_2$.

At 4 days after seeding, hMSC was induced by replacing the medium with adipogenic induction medium (Gibco Co.).

At 7 days after differentiation-induction, adipogenic inducing medium was removed from each support, washed with PBS, and then RNA was extracted immediately by using RNAisoPlus (Takara Co.).

The extracted RNA was reverse transcribed using RNA PCR kit (Takara), and the expression of early adipocytes marker PPARγ (Peroxisame Proliferator-Activated Receptor γ) and MSC marker CD105 was detected by PCR.

These markers are shown in FIG. 24. For comparison, markers for the adipocytes derived from differentiation-induced hMSC aggregates grown on petri dishs are shown as well.

Based on the result represented in FIG. 24, when the hMSC aggregate formed by limiting the size of the well were differentiation-induced, there was lower expression of CD105 and higher expression of PPARγ when the well opening size was smaller, suggesting that there was a adipogenic induction.

Next, at 10 days after differentiation-induction, the inducing medium was removed and the cells were washed with PBS, then fixed. The cells were stained with Oil red O, which is used for staining fat deposits in adipocytes.

The light microscopic images of cell staining are shown in FIG. 25.

The images represented in FIG. 25 indicate staining of the cell aggregate in the support well, which confirms the induction of adipocytes.

In addition, hMSCs were seeded and incubated in following cell culture supports; zirconia cell culture support lined with wells with opening size and depth of 70 μm, 175 μm, and 550 μm prepared with zirconia powder with average pore sizes of 0.6 to 0.9 μm and sintered at 1,150° C.; zirconia cell culture support lined with wells with opening size and depth of 70 μm, 175 μm, and 550 μm prepared with zirconia powder with average pore sizes of 0.6 to 0.9 μm and sintered at 1,050° C.; zirconia cell culture support lined with wells with opening size end depth of 70 μm, 175 μm, and 550 μm prepared with the zirconia powder with, average pore sizes of 0.75 to 12 μm presintered ax 1,150° C. and further sintered at 1,050° C., 1,150° C., and 1,250° C.; zirconia cell culture support lined with wells with opening size and depth of 70 μm, 175 μm, and 550 μm prepared with the zirconia powder with average pore sizes of 0.8 to 1.2 μm presintered at 1,250° C. and further sintered at 1,050° C., 1,150° C., and 1,250° C. As a result, the cell aggregates in each of the support well were stained with the dye, which confirmed the induction of adipocytes.

Comparative Example 7

Differentiation-induction of hMSC into Adipocytes on the Petri Dish

Immortalized hMSC at the density $7 \times 10^4$ cells were seeded on a gelatin coated petri dish with a diameter of 10 cm in a DMEM containing 10% PBS and incubated at 37° C. under 5% $CO_2$.

At 24 hours later, hMSC was induced by replacing the medium to adipogenic inducing medium (Gibco Co). The cell culture medium was replaced every 4 days.

At 7 days after differentiation-induction, differentiation-inducing medium was removed from each support, washed with. PBS, then immediately, RNA was extracted. The RNA extraction and detection of the markers by PCR was performed as previously described in Example 5.

These markers and the result from Example 5 are shown in FIG. 24.

Based on the result presented in FIG. 24, when the hMSC cultured on the petri dish was differentiation-induced, there was higher expression of CD105 when compared with the case where the cell culture support in Example 5 was used. In the case of PPARγ there was lower level of PPARγ expression when compared to using cell culture support with well opening size of 75 μm, 175 μm, and 350 μm in Example 5.

Therefore, the cell culture support in the present invention is proven to induce hMSC into adipocytes efficiently.

Next, 10 days after differentiation-induction. The differentiation-inducing medium was removed from the cell culture support. The cells were washed with PBS and fixed. The cells were stained with Oil red O, which is used for staining fat deposits in adipocytes.

The microscopic photos from cell staining are shown in FIG. 26.

According to the microscopic photos shown in FIG. 26, when hMSC were induced into adipocytes on the petri dish, few cells were stained with Oil red O even after 10 days of differentiation-induction. This result suggests that differentiation did not progress well.

Example 6

Differentiation-induction of hMSC into Osteoblasts

As described in Example 5, each support was sterilized and inserted into 24 well-plates. immortalized hMSC were seeded at the density of 1×10⁵ (a well opening size of 75 μm), 2×10⁵ (a well opening size of 175 μm), 3×10⁵ (a well opening size of 350 μm), 4×10⁵ (a well opening size of 510 μm) in DMEM containing 10% PBS. and incubated at 37° C. under 5% $CO_2$.

At 4 days after seeding the cells, the medium was replaced with osteogenic-inducing medium (GIBCO) for osteoblastic differentiation. The medium was replaced every 4 days.

At 14 days after differentiation-induction of the cells, the osteogenic induction medium was removed from the support, washed with PBS, then RNA was extracted by using RNAiso (Takara).

The extracted RNA was reverse transcribed using RNA PCR kit (Takara), and the expression of osteoblast markers, ColI (type I collagen), SppI (osteopontin) and MSC marker CD105 were detected by PCR.

These markers are shown in FIG. 27. For comparison, markers for the osteoblasts derived from differentiation-induced hMSC aggregates from petri dish are shown as well.

According to the result represented in FIG. 27, when the hMSC aggregate size was limited through the cell culture support well and was induced to differentiate, higher level of ColI and SppI were expressed as the well opening size was larger suggesting that an osteogenic-induction have occurred.

In addition, hMSCs were seeded and incubated in following cell culture supports: zirconia cell culture support lined with wells with opening size and depth of 70 μm, 175 μm, and 550 μm prepared with zirconia powder with average pore sizes of 0.6 to 0.9 μm and sintered at 1,150° C.; zircon/a cell culture support lined with wells with opening size and depth of 70 μm, 175 μm, and 550 μm prepared with zirconia powder with average pore sizes of 0.6 to 0.9 μm and sintered at 1,050° C.; zirconia cell culture support lined with wells with opening size and depth of 70 μm, 175 μm, and 550 μm prepared with the zirconia powder with average pore sizes of 0.75 to 1.2 μm presintered at 1,150° C. and further sintered at 1,050° C., 1,150° C., and 1,250° C.; zirconia cell culture support lined with wells with opening size and depth of 70 μm, 175 μm, and 550 μm prepared with the zirconia powder with average pore sizes of 0.8 to 1.2 μm presintered at 1,250° C. and further sintered at 1,050° C., 1,150° C., and 1,250° C. As a result, it has been confirmed that the osteogenic induction of hMSC aggregate is progressing inside the wells in each of the culture support.

Comparative Example 8

Osteogenic induction of hMSC on the Petri Dish

Immortalized hMSC at the density of 7×10⁴ were seeded on a gelatin coated petri dish (diameter 10 cm) in a DMEM containing 10% FBS and incubated at 37° C. under 5% $CO_2$.

After 24 hours, the medium was replaced with osteogenic-induction medium (GIBCO Co.) for osteoblastic differentiation. The medium was replaced every 4 days.

At 7 days after differentiation-induction of the cells, the osteogenic induction medium was removed from the support, washed with PBS, and then RNA was extracted immediately. The RNA extraction and detection of the markers by PCR was performed as described previously in Example 5.

These markers and the result from Example 6 are shown in FIG. 27.

According to the result represented in FIG. 27, when hMSC aggregate cultured on the petri dish was differentiation-induced, there was a higher expression of CD105 than cells from the cell culture supports described in Example 6. The expression of ColI and SppI was lower than using cell culture support with well opening size of 350 μm and 510 μm, which was described in Example 6.

Therefore, the cell culture support of the present invention confirmed the function of an effective osteogenic-induction.

While the invention has been described in detail with reference to specific embodiments thereof, it will be apparent to one skilled in the art that various changes and modifications can be made therein without departing from the spirit and scope thereof. Incidentally, the present application is based on Japanese Patent Applications No. 2010-178181 filed on Aug. 6, 2010, Japanese Patent Applications No 2011-130953 filed on Jun. 13, 2011 and the contents are incorporated herein by reference.

Also, all the references cited herein are incorporated as a whole.

What is claimed is:

1. A cell culture support for culturing mesenchymal stem cells, which comprises an upper surface of the cell culture support comprising a plurality of wells,
wherein the upper surface, which is a portion out of the well, has a root mean square roughness Rq of 100 to 280 nm and the number of a roughness curve crossing an average surface per 1 μm of a length of 1.6 to 3.0,
the cell culture support comprises sintered ceramics,
the upper surface is a non-processed surface after sintering of ceramics, and
a surface of the sintered ceramics has an average particle size of 0.6 to 1.2μm.

2. The cell culture support according to claim 1, wherein the well has a circular or rectangular opening and an opening size of 70 to 550 μm.

3. The cell culture support according to claim 1, wherein the well has a bottom surface and at least the bottom surface has a root mean square roughness Rq of 100 to 280 nm and the number of a roughness curve crossing an average surface per 1 μm of a length 1.6 to 3.0.

4. The cell culture support according to claim 1, wherein two central points of adjacent wells has a distance of 80 to 700 μm.

5. The cell culture support according to claim 1, wherein the ceramics is zirconia.

6. A method for culturing cells using the cell culture support according to claim 1, the method comprising;
disposing an upper surface of the cell culture support upwardly in a container;
supplying a first culture medium to the container to permeate the first culture medium by the capillary action to the well opening of the cell culture support;
adding a second culture medium comprising undifferentiated mesenchymal stem cells dropwise to the upper surface of the cell culture support into which the first culture medium is permeated to seed mesenchymal stem cells;
supplying the first culture medium to the container to immerse the cell culture support as a whole in the first culture medium and to proceed aggregation of the mesenchymal stem cells;
discharging the first culture medium and the second culture medium except for the mesenchymal stern cells out of the container; and
supplying a third culture medium for inducing differentiation of the mesenchymal stem cells which are aggregated into tissue cells to immerse the cell culture support as a whole in the third culture medium to induce differentiation of mesenchymal stem cells into any tissue cell of hyaline chondrocytes, adipocytes and osteoblasts in the well.

7. The method according to claim 6, wherein the number of mesenchymal stem cells in the second culture medium is from $1 \times 10^4$ to $1 \times 10^6$ per 1 cm$^2$ of the support.

8. The method according to claim 6, wherein the tissue cells are hyaline chondrocytes, adipocytes or osteoblasts.

9. The cell culture support according to claim 1, wherein a porosity of the sintered ceramics is from 10 to 50%.

10. The cell culture support according to claim 3, wherein the bottom surface of the well has a curved shape or a semicircular shape with a central portion depressed.

11. The cell culture support according to claim 9, wherein the sintered ceramics have an average pore size of 0.15 to 0.45 μm.

* * * * *